United States Patent
Oh et al.

(10) Patent No.: US 11,607,120 B2
(45) Date of Patent: Mar. 21, 2023

(54) CAPSULE ENDOSCOPIC RECEIVING DEVICE, CAPSULE ENDOSCOPE SYSTEM INCLUDING THE SAME, AND OPERATING METHOD OF CAPSULE ENDOSCOPIC RECEIVING DEVICE

(71) Applicant: ELECTRONICS AND TELECOMMUNICATIONS RESEARCH INSTITUTE, Daejeon (KR)

(72) Inventors: Kwang Il Oh, Daejeon (KR); Hyung-Il Park, Daejeon (KR); Tae Wook Kang, Daejeon (KR); Sung Eun Kim, Daejeon (KR); Mi Jeong Park, Sejong-si (KR); Jae-Jin Lee, Daejeon (KR); In Gi Lim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 958 days.

(21) Appl. No.: 16/378,472

(22) Filed: Apr. 8, 2019

(65) Prior Publication Data

US 2019/0307318 A1 Oct. 10, 2019

(30) Foreign Application Priority Data

Apr. 9, 2018 (KR) .......... 10-2018-0041257
Jul. 27, 2018 (KR) .......... 10-2018-0088190

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00006* (2013.01); *A61B 1/00016* (2013.01); *H04B 13/005* (2013.01); *A61B 5/0031* (2013.01)

(58) Field of Classification Search
CPC . A61B 1/041; A61B 1/00006; A61B 1/00009; A61B 1/00016; A61B 5/0031; H04B 13/005
See application file for complete search history.

(56) References Cited

U.S. PATENT DOCUMENTS 7,463,918 B2   12/2008   Kim et al.
8,160,672 B2   4/2012    Kim et al.
(Continued)

FOREIGN PATENT DOCUMENTS

JP              5265179 B2      8/2013
KR    10-2004-0068425 A        7/2004
(Continued)

*Primary Examiner* — Timothy J Neal
*Assistant Examiner* — William B Chou
(74) *Attorney, Agent, or Firm* — Rabin & Berdo, P.C.

(57) ABSTRACT

Provided are a capsule endoscopic receiving device, a capsule endoscope system including the same, and an operating method of the capsule endoscopic receiving device, the capsule endoscopic receiving device including an analog front end configured to receive a preamble from one receiving electrode pair from among a plurality of receiving electrodes, a valid signal detection circuit configured to compare a reference voltage with input data generated on a basis of a voltage level of the preamble, and a preamble processor configured to select a final electrode pair configured to receive the image data on a basis of a correlation value of the preamble and a comparison result of the input data and the reference voltage. According to the inventive concept, stability of receiving image data may be secured by selecting an optimal receiving electrode pair.

18 Claims, 13 Drawing Sheets

(51) Int. Cl.
*H04B 13/00* (2006.01)
*A61B 5/00* (2006.01)

(56) References Cited

U.S. PATENT DOCUMENTS

| | | | |
|---|---|---|---|
| 8,177,715 B2 | 5/2012 | Chiba et al. | |
| 8,224,244 B2 | 7/2012 | Kim et al. | |
| 8,798,049 B2 | 8/2014 | Lim et al. | |
| 2005/0183733 A1* | 8/2005 | Kawano | A61B 1/00156 607/116 |
| 2006/0173265 A1* | 8/2006 | Kim | A61B 5/06 600/407 |
| 2008/0227394 A1* | 9/2008 | Homan | A61B 5/0031 455/41.3 |
| 2008/0318541 A1* | 12/2008 | Kimoto | A61B 1/041 455/277.1 |
| 2009/0054731 A1* | 2/2009 | Shigemori | A61B 5/073 600/118 |
| 2009/0076352 A1* | 3/2009 | Fujita | A61B 1/00036 600/302 |
| 2009/0137883 A1* | 5/2009 | Chiba | A61B 1/041 600/302 |
| 2010/0130818 A1* | 5/2010 | Jung | A61B 1/00006 600/109 |
| 2010/0168517 A1* | 7/2010 | Shim | A61B 1/041 600/117 |
| 2011/0213205 A1* | 9/2011 | Uchiyama | A61B 34/73 600/118 |
| 2012/0201235 A1* | 8/2012 | Lim | A61B 1/041 370/349 |
| 2014/0139212 A1* | 5/2014 | Sakai | A61B 5/073 324/244 |
| 2014/0163357 A1* | 6/2014 | Higaki | A61B 5/061 600/424 |
| 2018/0026729 A1 | 1/2018 | Lim et al. | |
| 2019/0090721 A1* | 3/2019 | Koide | A61B 1/041 |

FOREIGN PATENT DOCUMENTS

| | | |
|---|---|---|
| KR | 10-0522132 B1 | 10/2005 |
| KR | 10-1063859 B1 | 9/2011 |
| KR | 10-1803317 B1 | 12/2017 |

* cited by examiner

CAPSULE ENDOSCOPIC RECEIVING DEVICE, CAPSULE ENDOSCOPE SYSTEM INCLUDING THE SAME, AND OPERATING METHOD OF CAPSULE ENDOSCOPIC RECEIVING DEVICE

CROSS-REFERENCE TO RELATED APPLICATIONS

This U.S. non-provisional patent application claims priority under 35 U.S.C. § 119 of Korean Patent Application Nos. 10-2018-0041257, filed on Apr. 9, 2018, and 10-2018-0088190, filed on Jul. 27, 2018, the entire contents of which are hereby incorporated by reference.

BACKGROUND

The present disclosure herein relates to a communication system using a human body as a material, and more particularly, to a capsule endoscopic receiving device, a capsule endoscope system including the same, and an operating method of the capsule endoscopic receiving device.

An endoscope is a device inserted into the inside of a human body and configured to capture an image of the inside of an organ and externally transfer the image. A typical wired endoscope is disadvantageous in that the viewing distance range of the endoscope is limited to the length of the wire of the endoscope, and causes inconvenience to a user at the time of inserting through the oral cavity or the anal passage. Accordingly, a capsule endoscope has emerged which may wirelessly transfer the captured image. Since such a capsule endoscope transmits and receives a signal in a wireless manner, it is advantageous in that the limitation on movement path is reduced, the inconvenience of the user is solved to increase an inspection time, and convenience of inspection is increased.

As a communication scheme of the capsule endoscope, a human body communication manner is emerging in which a signal or information is transferred through a human body that is adopted as a communication material. A capsule endoscope system in a human body communication scheme uses a human body as a material and thus does not require a separate signal transfer medium. Accordingly, in comparison to the typical wireless communication scheme, the capsule endoscope system has a binding force on a signal and does not require an RF circuit, an antenna, or the like, and may be implemented in low power. However, in order to perform the human body communication, the capsule endoscope and a capsule endoscopic receiving device are required to contact the human body.

The capsule endoscope may continuously move due to the peristalsis of a digestive organ. Accordingly, relative positions between the capsule endoscope and the capsule endoscopic receiving device may be continuously changed. In order to actively countermeasure such a change, the capsule endoscopic receiving device may include a plurality of receiving electrodes attached to various parts of the human body. In addition, it is also necessary to find a combination of the receiving electrodes that may stably receive an image in correspondence to the continuously moving capsule endoscope.

SUMMARY

The present disclosure provides a capsule endoscopic receiving device configured to stably and effectively receive image data provided from the capsule endoscope, a capsule endoscope system including the same, and an operation method of the capsule endoscopic receiving device.

An embodiment of the inventive concept provides a capsule endoscopic receiving device including: an analog front end configured to receive a preamble from one receiving electrode pair from among a plurality of receiving electrodes; a valid signal detection circuit configured to compare a reference voltage with input data generated on a basis of a voltage level of the preamble; and a preamble processor configured to select a final electrode pair configured to receive the image data on a basis of a correlation value of the preamble and a comparison result of the input data and the reference voltage.

In an embodiment, when the input data is larger than the reference voltage, the valid signal detection circuit may output pulses to the preamble processor. On the basis of the number of pulses, the preamble processor may determine validity of a receiving electrode pair corresponding to the preamble and may select the final electrode pair from among receiving electrode pairs having the validity. In an embodiment, the preamble processor may select, as the final electrode pair, a receiving electrode pair corresponding to a preamble having a largest correlation value from among the receiving electrode pairs having the validity.

In an embodiment, the valid signal detection circuit may include: an amplifier configured to output the pulses on a basis of the input data and the reference voltage; a diode configured to provide a voltage generated on the basis of the pulses or the reference voltage to the amplifier; and a capacitor configured to store the voltage. When the pulses are output, the voltage may be generated on the basis of a peak value of the pulses, and when the pulses are not output, the voltage may be the reference voltage. To this end, the valid signal detection circuit may further include: a first switch configured to electrically connect the capacitor and the diode, while the receiving electrode pair receives the preamble; and a second switch configured to provide the reference voltage to the capacitor, while the receiving electrode pair does not receive the preamble.

In an embodiment, the valid signal detection circuit may include a comparator configured to generate the pulses, when the input data is larger than the reference voltage.

In an embodiment, the preamble processor may include: a pulse counter configured to count a number of pulses; a pulse comparator configured to compare the number of pulses and a reference number; a correlator configured to calculate the correlation value on a basis of a similarity between the preamble and a reference preamble; and a receiving electrode controller configured to generate a selection signal for selecting the final electrode pair on a basis of the correlation value and a result of comparing the number of pulses with the reference number.

In an embodiment, the capsule endoscopic receiving device may further include a second valid signal detection circuit configured to compare the input data with a second reference voltage that is different from the reference voltage, and the preamble processor may select the final electrode pair further on a basis of a result of comparing the input data with the second reference voltage.

In an embodiment of the inventive concept, a capsule endoscope system includes: a capsule endoscopic transmission device configured to generate a preamble and image data; and a capsule endoscopic receiving device configured to receive the preamble through a living body for each receiving electrode pair combination for a plurality of receiving electrodes, and to select a final electrode pair configured to receive the image data on a basis of a received voltage level of the preamble and a correlation value of the preamble.

In an embodiment of the inventive concept, an operation method of a capsule endoscopic receiving device, the operation method includes: selecting a first receiving electrode pair from among a plurality of receiving electrodes during a first switching time; receiving a preamble generated from a capsule endoscope through the first receiving electrode pair during a preamble reception time after the first switch time; determining validity of the preamble on a basis of a voltage level of the preamble received through the first receiving electrode pair; calculating a correlation value corresponding to the first receiving electrode pair on a basis of a similarity between the preamble received through the first receiving electrode pair and a reference preamble; selecting a second receiving electrode pair that is different from the first receiving electrode pair during a second switching time after the preamble reception time; and selecting a final electrode pair from among the plurality of receiving electrodes on a basis of the validity and the correlation value.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Hereinafter, an exemplary embodiment of the present disclosure will be described in detail with reference to the accompanying drawings such that a person skilled in the art may easily carry out the embodiments of the present disclosure.

Hereinafter, a series of processes are described in which a signal, data, or a frame transmitted from a capsule endoscopic transmission device is provided to a capsule endoscopic receiving device. Such a signal, data and a frame may be modulated, combined or transformed by the capsule endoscopic transmission device, may be distorted or attenuated in a communication process, and may be demodulated, separated, or recovered by the capsule endoscope receiving device. When it is said that intrinsic information in the signal, data or frame is maintained and only a formal deformation occurs, one term may be used for convenience of explanation. For example, it may be understood that descriptions will be consistently provided with image data, when the intrinsic information is not changed, even when the image data is modified in the capsule endoscopic transmission device, distorted and attenuated in a human body, and recovered in the receiving device, and thus only a formal deformation occurs in the image data.

Figure 1:
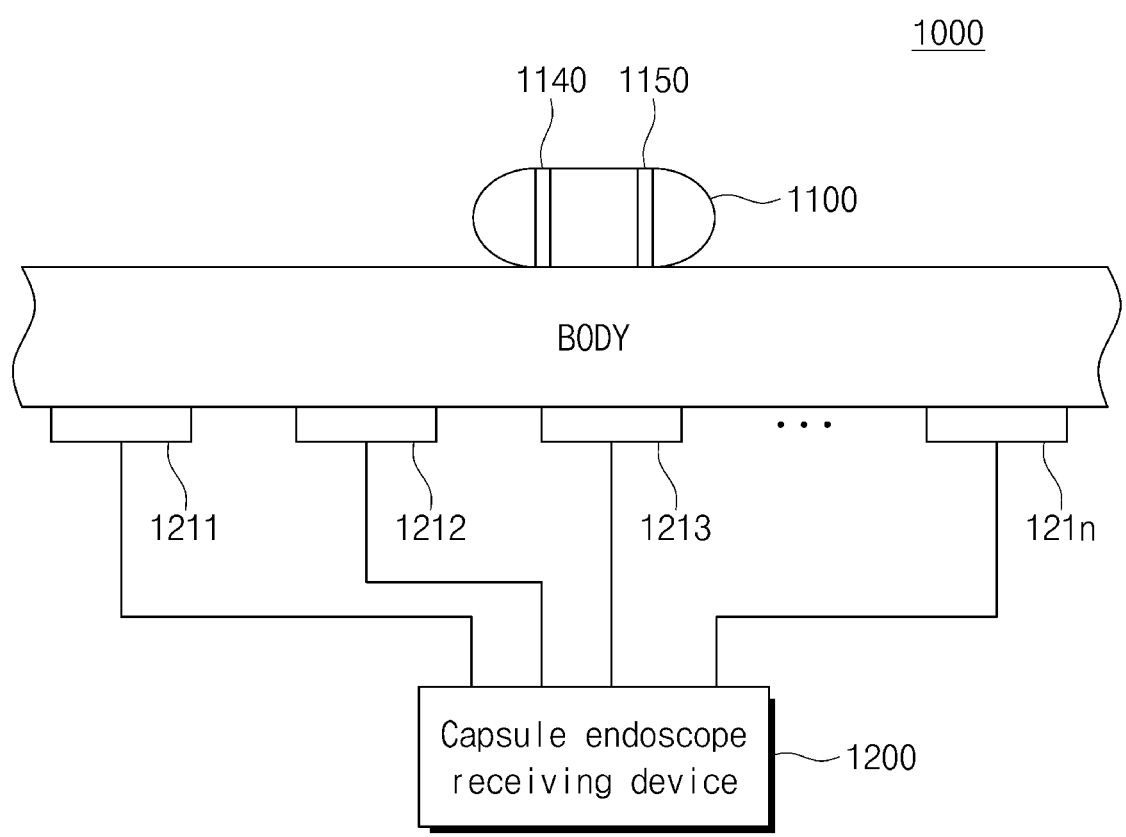
FIG. 1 illustrates a capsule endoscope system according to an embodiment of the inventive concept.

FIG. 1 illustrates a capsule endoscope system according to an embodiment of the inventive concept. In relation to FIG. 1, the capsule endoscope system 100 includes a capsule endoscopic transmission device 1100 (hereinafter, capsule endoscope) and a capsule endoscopic receiving device 1200. The capsule endoscope system 1000 transfers a signal or information by adopting a human body as a medium. Hereinafter, it will be described that the capsule endoscope system 1000 performs a communication using the human body, but the transfer material of the signal or information is not limited to the human body, but various living bodies such as an animal may be employed as the medium.

The capsule endoscope 1100 may be inserted inside the human body through an intake. The capsule endoscope 1100 may capture an image of the inside of the human body such as a digestive organ, and generate image data on the basis of the captured image. The image data may be transferred to the capsule endoscopic receiving device 1200 via the material of the human body BODY. When the capsule endoscope 1100 contacts the human body BODY or is separated therefrom with a small interval, the image data may be provided to the capsule endoscopic receiving device 1200. Here, the small interval may mean a reference distance over which the image data may reach with the magnitude identifiable by the capsule endoscopic receiving device 1200.

The capsule endoscope 1100 may include a transmission electrode 1140 for transmitting the image data and an earth electrode 1150. The capsule endoscope 1100 may transmit the image data in a differential signal type using the transmission electrode 1140 and the earth electrode 1150. A current due to the potential difference between the transmission electrode 1140 and the earth electrode 1150 may be provided to the capsule endoscopic receiving device 1200 through the human body BODY.

The capsule endoscope 1100 may transmit a preamble to the capsule endoscopic receiving device 1200 before transmitting the image data. The capsule endoscope 1100 continuously moves inside the human body. A reception sensitivity of the signal or data transmitted by the capsule endoscope 1100 may depend on the position or orientation of the capsule endoscope 1100. In detail, the reception sensitivity of the data may depend on relative positions and orientations between the capsule endoscope 1100 and a plurality of receiving electrodes 1211 to 121n. The preamble may be used for selecting an optimal receiving electrode pair for receiving the image data from among combinations of the plurality of receiving electrodes 1211 to 121n. A detailed description thereabout will be provided later.

The capsule endoscopic receiving device 1200 includes a plurality of electrodes 1211 to 121n for receiving the preamble and image data. The plurality of receiving electrodes 1211 to 121n may be separately attached to different parts of the human body BODY. Two receiving electrodes of the plurality of receiving electrodes 1211 to 121n may be selected as one receiving electrode pair, and the preamble and image data may be received through the selected receiving electrode pair. In other words, the preamble and image data may be received as a differential signal through the selected receiving electrode pair.

The capsule endoscopic receiving device 1200 may select the optimal receiving electrode pair (final electrode pair) for receiving the image data using the preamble. The capsule endoscopic receiving device 1200 may receive the preamble for each receiving electrode pair combination. The capsule endoscope receiving pair 1200 may determine validity of the receiving electrode pair according to a voltage level of the preamble received for each receiving electrode pair. For example, when the voltage level of the received preamble is larger than (or equal to) a reference voltage for a prescribed time or with a prescribed frequency, it may be determined that the receiving electrode pair receiving the preamble is valid. The preamble may be attenuated during a transfer through the human body BODY. The reference voltage may be set on the basis of the minimum voltage level at which the image data attenuated and provided to the capsule endoscopic receiving device 1200 may be identified and processed.

In addition, the capsule endoscopic receiving device 1200 may calculate a correlation value of the received preamble. The correlation value may be calculated on the basis of a similarity between the received preamble and a preset reference preamble. The capsule endoscopic receiving device 1200 may compare the pattern of the preamble received from the selected receiving electrode pair with the pattern of the reference preamble to calculate the correlation value. The reference preamble may have the same pattern as the preamble transmitted by the capsule endoscope 1100. The preamble may be distorted during the transfer through the human body BODY. The correlation value may be used for determining a degree of distortion in a data transmission process.

The capsule endoscopic receiving device 1200 may select the final electrode pair for receiving the image data on the basis of the validity of the preamble and the correlation value. The capsule endoscopic receiving device 1200 may determine the validity and calculate the correlation value for each combination of the plurality of receiving electrodes 1211 to 121n. When the number of receiving electrodes is n, the number of such combinations may be $_nC_2$. The capsule endoscopic receiving device 1200 may change a receiving electrode pair $_nC_2$ times, and determine the validity and the correlation value. The capsule endoscopic receiving device 1200 may select the final electrode pair from among the receiving electrode pairs having the validity. For example, the capsule endoscopic receiving device 1200 may select, as the final electrode pair, the receiving electrode pair that has received the preamble having the largest correlation value from among the receiving electrode pairs having the validity.

Figure 2:
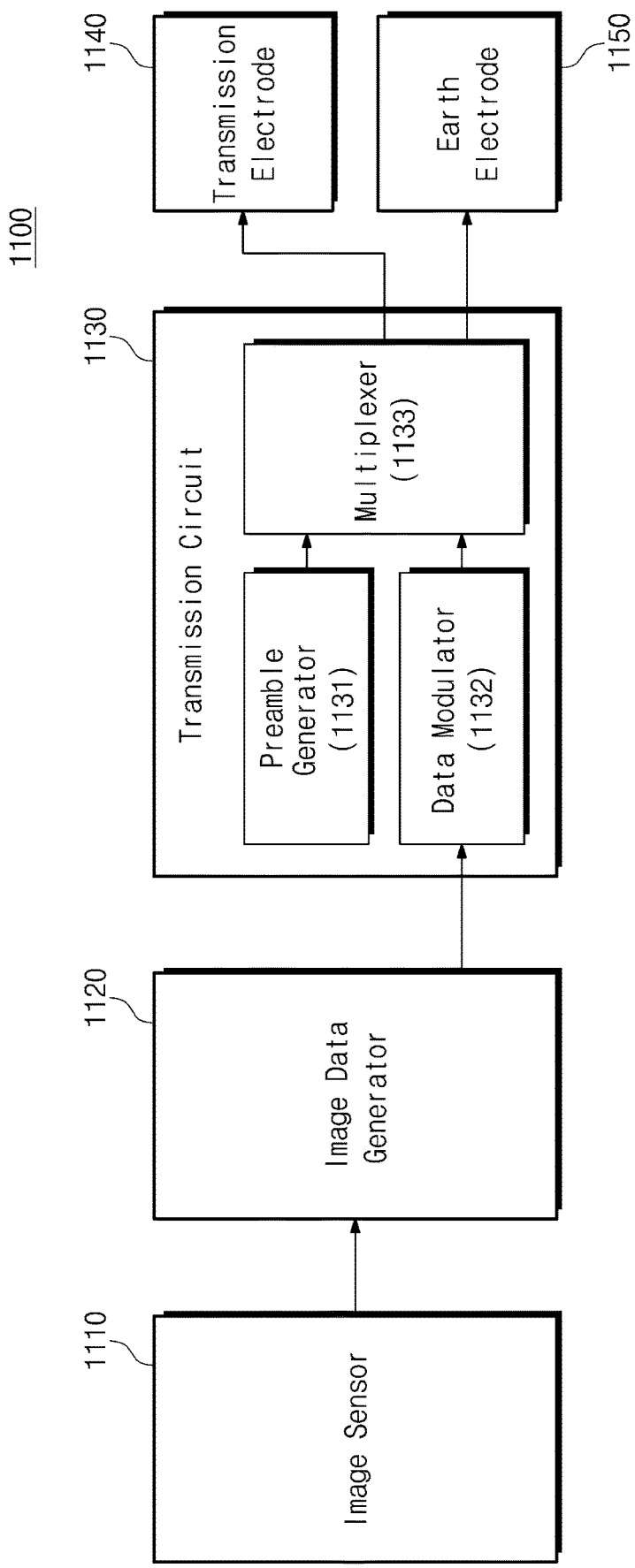
FIG. 2 is an exemplary block diagram of a capsule endoscope of FIG. 1.

FIG. 2 is an exemplary block diagram of the capsule endoscope of FIG. 1. In relation to FIG. 2, the capsule endoscope 1100 includes an image sensor 1110, an image data generator 1120, a transmission circuit 1130, a transmission electrode 1140, and an earth electrode 1150. The transmission electrode 1140 and the earth electrode 1150 respectively correspond to the transmission electrode 1140 and the earth electrode 1150 of FIG. 1. The capsule endoscope 1100 shown in FIG. 2 may be understood as one embodiment in which a preamble and image data are transmitted, and the capsule endoscope 1100 in FIG. 1 is not limited to the structure of FIG. 2.

The image sensor 1110 may capture an image inside an organ and generate image data. The image sensor 1110 may be a charge coupled device (CCD) or a CMOS image sensor, but is not limited thereto. For example, the image sensor 1110 may include a pixel array configured to sense external light to convert the light into an electrical signal, and an analog-to-digital converter configured to convert the electrical signal to the image data that is a digital signal.

The image data generator 1120 generates an image frame on the basis of the image data generated by the image sensor 1110. The image data generator 1120 receives the image data from the image sensor 1110. The image data generator 1120 may add image information to the image data to generate the image frame. For example, the image information may include line information or the like corresponding to a pixel in which an image signal is generated.

The transmission circuit 1130 combines the image frame (data frame) and a control frame to generate a transmission frame. The image frame includes the image data, and the control frame includes the preamble. The transmission frame may be provided to the capsule endoscopic receiving device 1200 of FIG. 1 through the transmission electrode 1140. To this end, the transmission circuit 1130 may include a preamble generator 1131, a data modulator 1132, and a multiplexer 1133.

The preamble generator 1131 may generate the preamble used for selecting the final electrode pair through which the image data is received. The preamble may play a role of informing data frame transmission before the image data is transmitted. In order to determine the validity and the correlation value for each receiving electrode pair, the preamble may be divided into a plurality of preambles respectively corresponding to the receiving electrode pair, and the number of divided preambles may correspond to the number of the receiving electrode pair combinations. A switching time may be provided between the plurality of preambles. The switching time may be provided so as to secure a time for changing the receiving electrode pair. The preamble may have the specific pattern in order to calculate the correlation value, and the patterns and voltage levels of the divided preambles may be the same.

The data modulator 1132 modulates the image frame. The data modulator 1132 receives the image frame from the image data generator 1120. The data modulator 1132 may modulate the image frame according to a preset modulation scheme. For example, the data modulator 1132 may modulate the image frame in a frequency selective digital transmission (FSDT) manner using a frequency selective spreading code.

The multiplexer 1133 generates the transmission frame and transfers the transmission frame to the capsule endoscopic receiving device 1200 using the transmission electrode 1140 and the earth electrode 1150. The multiplexer 1133 receives the preamble and the modulated image frame. The multiplexer 1133 adds the switching time between the plurality of preambles generated by the preamble generator 1131 to generate the control frame. The modulator 1133 may add, to the image frame, a line sync, a header, a cyclic redundancy check (CRC), or the like to generate the data frame. Although not shown in the FIG. 2, the transmission circuit 1130 may further include a separate component configured to generate the line sync, the header or the CRC. The multiplexer 1133 externally transmits the transmission frame including the control frame and data frame through the transmission electrode 1140. The transmission frame may be a digital signal.

Figure 3:
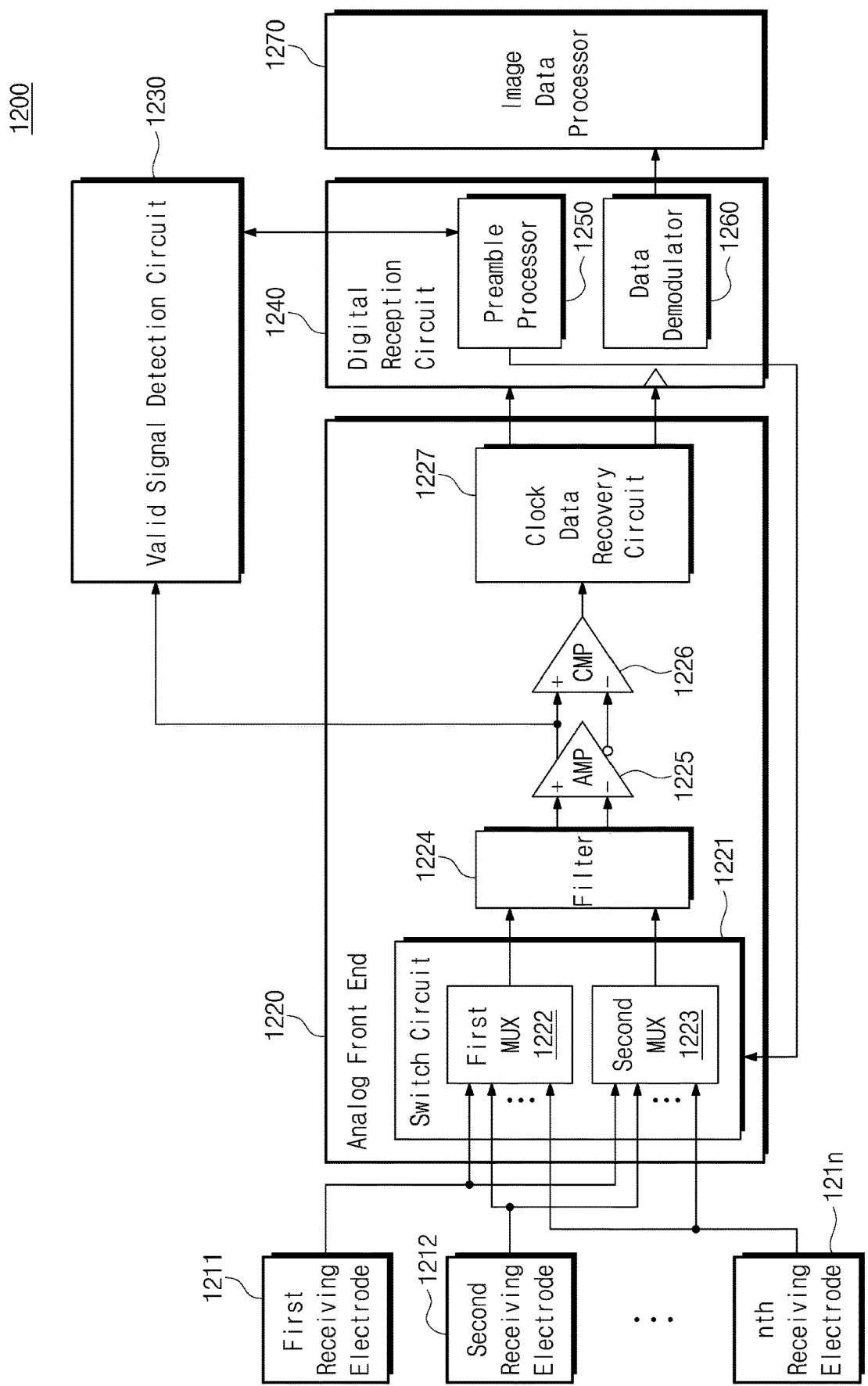
FIG. 3 is an exemplary block diagram of a capsule endoscopic receiving device of FIG. 1.

FIG. 3 is an exemplary block diagram of the capsule endoscopic receiving device of FIG. 1. In relation to FIG. 3, the capsule endoscopic receiving device 1200 includes first to nth receiving electrodes 1211 to 121*n*, an analog front end 1220, a valid signal detection circuit 1230, a digital reception circuit 1240, and an image data processor 1270. The first to nth receiving electrodes 1211 to 121*n* correspond to the plurality of receiving electrodes 1211 to 121*n* of FIG. 1. The capsule endoscope 1200 shown in FIG. 3 may be understood as one embodiment in which the receiving electrode pair is selected through the correlation value and the validity of the preamble, and the capsule endoscope 1200 of FIG. 1 is not limited to the structure of FIG. 3.

Two receiving electrodes (receiving electrode pair) selected from among the first to nth receiving electrodes 1211 to 121*n* receive the transmission frame. The first to nth receiving electrodes 1211 to 121*n* may receive the control frame for each receiving electrode pair combination. The preamble divided for each receiving electrode pair combination is received. For example, when n is 8, the receiving electrode pairs may have 28 combinations, and 28 divided preambles may be respectively received for the receiving electrode pair combinations to be provided to the analog front end 1220. As a result of receiving the preamble for each receiving electrode pair combination, the final electrode pair is selected, and the data frame including the image data may be received through the final electrode pair.

The analog front end 1220 may filter, amplify, and recover the transmission frame received through the selected receiving electrode pair. To this end, the analog-front end 1220 may include a switch circuit 1221, a filter 1224, an amplifier 1225, a comparator 1226, and a clock and data recovery (CDR) circuit 1227.

The switch circuit 1221 may receive the transmission frame through the selected receiving electrode pair. The switch circuit 1221 may receive the preamble for each receiving electrode pair combination. The switch circuit 1221 may receive the image data through the final receiving electrode pair selected as a result of analyzing the preamble. The switch circuit 1221 may be electrically connected with two receiving electrodes among the first to nth receiving electrodes 1211 to 121*n* to receive the transmission frame on the basis of a selection signal from the digital reception circuit 1240.

The switch circuit 1221 may include a first multiplexer 1222 configured to select one receiving electrode between the two receiving electrodes, and a second multiplexer 1223 configured to select the other receiving electrode. The first and second multiplexers 1222 and 1223 may be electrically and respectively connected the selected receiving electrodes to receive the preamble or image data provided through the human body BODY as a differential signal. The first and second multiplexers 1222 and 1223 are electrically connected to different receiving electrodes.

When receiving the preamble, the switch circuit 1221 may change a receiving electrode pair to be selected as many as the number of the receiving electrode pair combinations. For example, while the first multiplexer 1222 is connected with the first receiving electrode 1211, the second multiplexer 1223 may be sequentially connected with the second to nth electrodes 1212 to 121*n*. Then, while the first multiplexer 1222 is connected with the second receiving electrode 1212, the second multiplexer 1223 may be sequentially connected with the third to nth electrodes 1213 to 121*n*. Such a receiving electrode pair may be changed till the first multiplexer 1222 is connected with the (n−1)th receiving electrode and the second multiplexer 1223 is connected with the nth receiving electrode 121*n*.

The filter 1224 may remove a noise or the like of the received preamble or image data. For example, the filter 1224 may be a band pass filter, but is not limited thereto. The filter 1224 may pass a frequency band of the preamble or image data set in the capsule endoscope 1100 of FIG. 1, and cut off the remaining frequency bands.

The amplifier 1225 may amplify the filtered preamble or image data. The preamble or image data may be received as the differential signal by the selected receiving electrode pair. The signal received through the first multiplexer 1222 may be provided to a positive input terminal of the amplifier 1225 through the filter 1224. The signal received through the second multiplexer 1223 may be provided to a negative input terminal of the amplifier 1225 through the filter 1224. The potential difference between the positive input terminal and the negative input terminal may be amplified to be provided to the comparator 1226 as a differential signal. In addition, at the time of receiving the preamble, an output of the amplifier 1225 may be provided to the valid signal detection circuit 1230 in order to determine the validity of the preamble. For convenience of explanation, the output of the amplifier 1225, which is to be provided to the valid signal detection circuit 1230, may be referred to as input data.

The comparator 1226 may convert the differential signal amplified by the amplifier 1225 into a single phase signal to be provided to the CDR circuit 1227. The comparator 1226 may convert the amplified preamble or image data to the single phase signal in order to recover the clock and data. As described above, the transmission frame including the preamble and image data, which are provided through the human body BODY, may be a digital signal, and the analog front end 1220 may not include a separate analog-to-digital converter.

The CDR circuit 1227 may process the received transmission frame so as to be matched with the transmission frame generated in the capsule endoscope 1100 of FIG. 1. The CDR circuit 1227 may separate data and a clock from the preamble or image data provided through the filter 1224, the amplifier 1225, and the comparator 1226. The separated data and clock may be provided to the digital reception circuit 1240.

The valid signal detection circuit 1230 may be used for determining the validity of the preamble or the receiving electrode pair that has received the preamble on the basis of the voltage level of the preamble. The valid signal detection circuit 1230 may receive input data that is generated by amplifying the preamble by the amplifier 1225. The valid signal detection circuit 1230 may compare the input data with the reference voltage. For example when the input data has a higher voltage level than the reference voltage, the valid signal detection circuit 1230 may generate a pulse (or pulses) and output the generated pulse(s) to the digital reception circuit 1240. The validity of the preamble or the receiving electrode pair that has received the preamble may be determined according to the number of pulses. The detailed structure and the operation of the valid signal detection circuit 1230 will be described later.

Unlike the FIG. 3, the valid signal detection circuit 1230 may be provided in plurality. For example, a first valid signal detection circuit may compare the input data with a first reference voltage to generate pulses, and a second valid signal detection circuit may compare the input data with a second reference voltage to generate pulses. The first reference voltage and the second reference voltage may have different voltage levels. For example, the first reference voltage may have a higher voltage level than the second reference voltage. In this case, according to the comparison result of the first reference voltage and the input data, the validity of each of the receiving electrode pairs may be determined. When there is not the input data having a higher voltage level than the first reference voltage, the validity of each electrode pair may be determined according the comparison result of the second reference voltage and the input data. In other words, a plurality of reference voltages are provided, and thus an optimal receiving electrode pair configured to receive the image data may be selected, even when the reception sensitivity is low.

The digital reception circuit 1240 may analyze the preamble to select the final electrode pair that will receive the image data. The image data received through the final electrode pair may be demodulated in the digital reception circuit 1240 and be provided to the image data processor 1270. To this end, the digital reception circuit 1240 may include a preamble processor 1250 and a data demodulator 1260.

The preamble processor 1250 selects the optimal receiving electrode pair configured to receive the image data. The preamble processor 1250 may determine the validity of the preamble received for each receiving electrode pair, and calculate the correlation value. The preamble processor 1250 may generate a selection signal for continuously changing the receiving electrode pair in order to receive the preamble for each receiving electrode pair. The generated selection signal may be provided to the switch circuit 1221. The preamble processor 1250 may receive the generated pulses from the valid signal detection circuit 1230 in order to determine the validity of the preamble or the receiving electrode pair having received the preamble. Here, according to the embodiment, the valid signal detection circuit 1230 may compare the input data with the reference voltage to generate the pulses under a control of the preamble processor 1250.

The preamble processor 1250 may count the number of pulses provided from the valid signal detection circuit 1230. When the counted number of pulses is present within a reference range, the preamble processor 1250 may determine the receiving electrode pair to be valid. Here, the reference range may have both a lower limit and an upper limit, but is not limited thereto. The lower limit of the number of pulses may be defined as the number of pulses that may be generated at the minimum voltage level at which the image data may be identified and processed. The upper limit of the number of pulses may be defined as the maximum number of pulses that may be generated, when the preamble is normally received under a condition that a noise or the like is not generated.

The preamble processor 1250 may calculate the correlation value of the preamble. The preamble processor 1250 may compare the pattern of the preamble received for each electrode pair and the pattern of the reference preamble. The preamble processor 1250 may calculate the correlation value on the basis of the similarity between the received preamble and the reference preamble. For example, as the similarity is higher, the correlation value may be large. In order to calculate the correlation value, the preamble processor 1250 may receive, from the analog front end 1220, the preamble from which the data and clock are separated.

The preamble processor 1250 may select the final electrode pair on the basis of the validity for each receiving electrode pair and the calculated correlation value. The preamble processor 1250 may select the final electrode pair from among the receiving electrode pairs having the validity. For example, the preamble processor 1250 may select a receiving electrode pair that has received the preamble having the highest correlation value from among the receiving electrode pairs having the validity. However, the embodiment of the inventive concept is not limited thereto, and the preamble processor 1250 may select the final electrode pair in various ways on the basis of the validity and the correlation value. For example, when the receiving electrode pair, which has received the preamble having the highest correlation value among the receiving electrode pairs having the validity, is in plurality, the final electrode pair may be arbitrarily selected from among the receiving electrode pairs that satisfy two conditions. The preamble processor 1250 may generate a selection signal for selecting the final electrode pair, and provide the selection signal to the switch circuit 1221.

The data demodulator 1260 may demodulate the recovered image data (image frame) recovered from the clock data recovery circuit 1227. The data demodulator 1260 may demodulate the image data in correspondence to the modulation scheme of the capsule endoscope 1100. The demodulated image data is provided to the image data processor 1270.

The image data processor 1270 may process the demodulated image data (image frame) so that the processed data is suitable to be provided to the user. For example, the image data processor 1270 may process the image data in a type in which the image is to be displayed on a display device (not shown).

Figure 4:
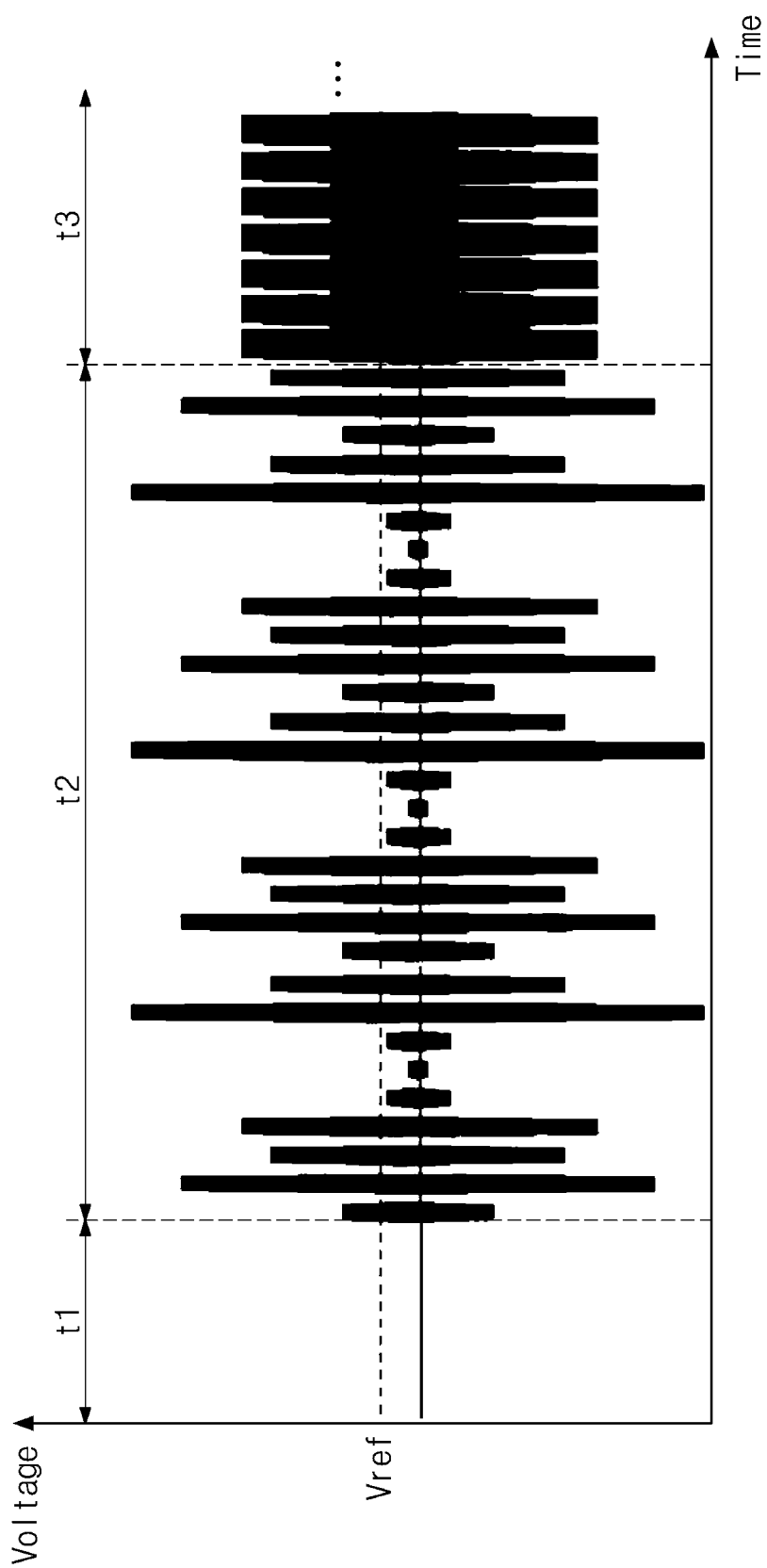
FIG. 4 is a graph for explaining a preamble and image data provided to the capsule endoscopic receiving device of FIG. 3.

FIG. 4 is a graph for explaining the preamble and image data provided to the capsule endoscopic receiving device of FIG. 3. In relation to FIG. 4, a horizontal axis may denote time, and a vertical axis may denote the voltage level of the input preamble or image data. An operation time of the capsule endoscopic receiving device 1200 of FIG. 3 may be divided into a first time t1 during which the preamble or image data is not received, a second time t2 during which the preamble is received, and a third time t3 during which the image data is received. For convenience of explanation, FIG. 4 will be described in relation to the reference numerals of FIG. 3.

During the second time t2, the capsule endoscopic receiving device 1200 may receive the control frame including the preamble. During the second time t2, the capsule endoscopic receiving device 1200 may receive the preamble for each receiving electrode pair combination to select the final electrode pair. When the number of receiving electrodes is 8, the receiving electrode pair combinations may be 28. The switch circuit 1221 may receive the preamble for each of the 28 receiving electrode pair combinations under a control of the preamble processor 1250.

During the second time t2, it is illustrated that the capsule endoscopic receiving device 1200 may receive a signal 30 times, and a period in which the signal is not received is present between periods in which the signal is received. For example, the capsule endoscopic receiving device 1200 may receive the preamble 28 times for the receiving electrode pair combinations. The preamble to be received 28 times may be 28 divided preambles generated by the capsule endoscope 1100 of FIG. 1. In addition, for example, the last two periods may be a time for selecting the final electrode pair. The period in which the signal is not received between the periods in which the signal is received 30 times may be a time for changing the receiving electrode pair configured to receive the preamble. Such a time corresponds to a switching time provided between the preambles divided by the capsule endoscope 1100 of FIG. 1.

Since positions at which the receiving electrodes contact the human body are different from each other, the preamble may be received according to a different reception sensitivity or attenuation rate for each receiving electrode pair. The reception sensitivity may depend on the relative distance or orientation between the capsule endoscope 1100 and the capsule endoscopic receiving device 1200. When the received preamble has a higher voltage level than a reference voltage Vref, the receiving electrode pair having received the corresponding preamble may be determined to be valid. For example, in FIG. 4, the receiving electrode pairs having received first to fourth preambles may be determined to be valid.

During the third time t3, the capsule endoscopic receiving device 1200 may receive the image frame including the image data through the final electrode pair selected during the second time t2. The capsule endoscopic receiving device 1200 may select the final electrode pair in consideration of not only the voltage level of the preamble, but also the correlation value through the pattern of the received preamble.

When the final electrode pair is selected only in consideration of the correlation value of the preamble, the voltage level of the receive image data may be smaller than the reference voltage Vref. In this case, the image data processor 1270 may not identify the image data and may not provide an image to the user. In addition, when the final electrode pair is selected only in consideration of the voltage level of the preamble, there is a possibility that the received image data is distorted. In this case, the image displayed to the user may be distorted unlike the actual image. In other words, since the final electrode pair selected according to an embodiment of the inventive concept considers both the attenuation and distortion, the reliability of the displayed image may be secured.

Figure 5:
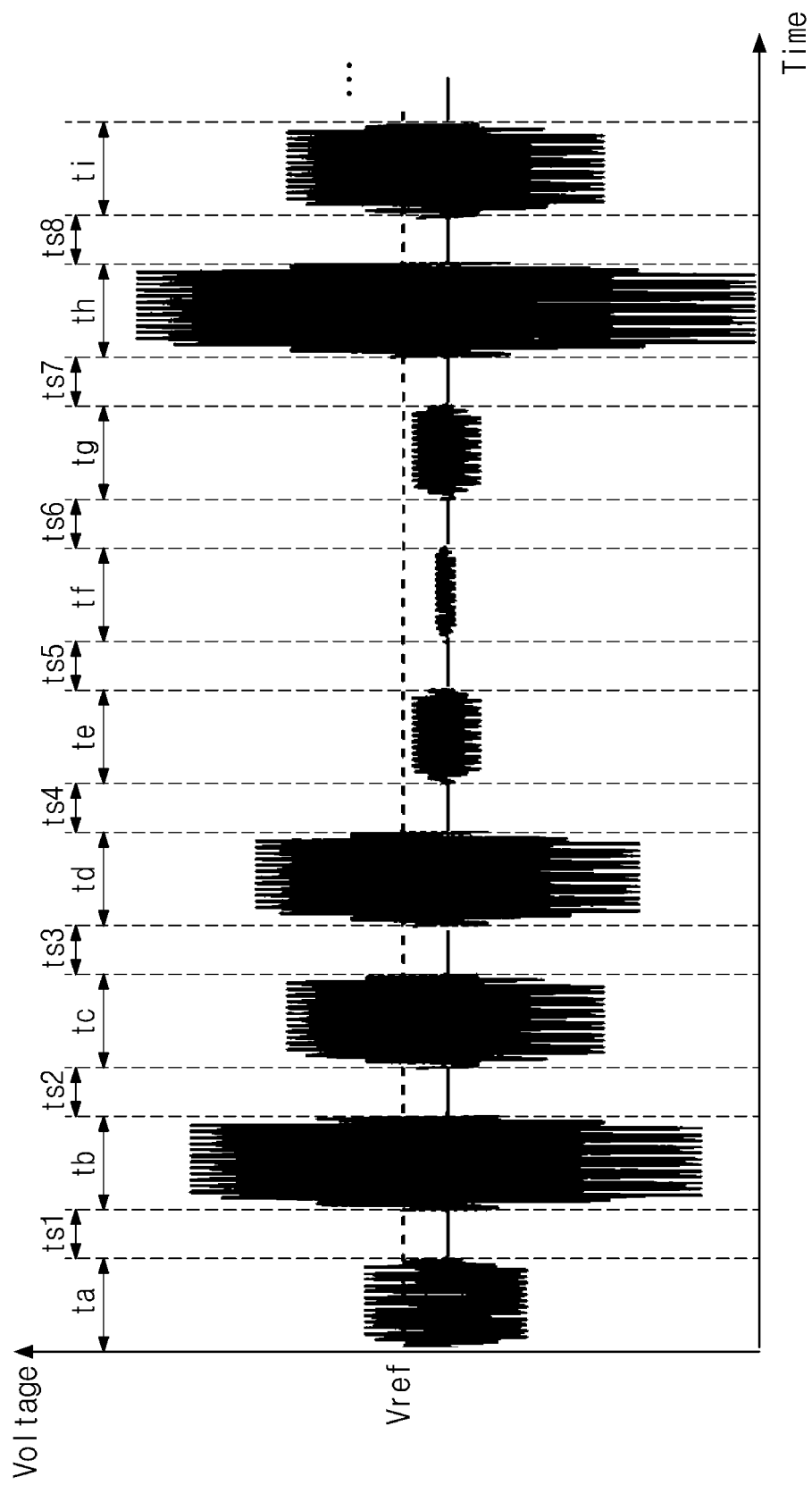
FIG. 5 is a graph illustrated by extending a time for receiving the preamble of FIG. 4.

FIG. 5 is a graph illustrated by extending a time for receiving the preamble of FIG. 4. In relation to FIG. 5, a horizontal axis may denote time, and a vertical axis may denote the voltage level of the input preamble. The time shown in FIG. 5 may be understood as a part of the second time t2 of FIG. 4. The second time t2 may be divided into preamble reception times ta to ti and the switching times ts1 to ts8. For convenience of explanation, FIG. 5 will be described with reference to the reference numerals of FIG. 3.

At each of the preamble reception times ta to ti, the capsule endoscopic receiving device 1200 may receive preambles for different receiving electrode pair combinations. For example, at the first preamble reception time ta, the preamble may be received through a first receiving electrode 1211 and a second receiving electrode 1212. When the number of receiving electrodes is 8, at first to eighth preamble reception times ta to th, the capsule endoscopic receiving device 1200 may receive the preamble by fixing the first receiving electrode 1211, and sequentially changing the second to eighth receiving electrodes. Then, at a ninth preamble reception time ti, the preamble may be received through the second and third receiving electrodes.

The preambles respectively received at the preamble reception times ta to ti may have an identical voltage level at the time of being generated in the capsule endoscope. In other words, according to the selected receiving electrode pairs, the reception sensitivity varies and the voltage level of the received preamble may become different. The capsule endoscopic receiving device 1200 may determine, as valid, the preamble having a peak value larger than (or equal to) the reference voltage Vref. In FIG. 5, the receiving electrode pairs selected at the first to fourth preamble reception times ta to td and the eighth and ninth preamble reception times th and ti may be determined to be valid. The final electrode pair may be selected from among the receiving electrode pairs determined to be valid.

At each of switching times ts1 to ts8, the capsule endoscopic receiving device 1200 changes the receiving electrode pair combination. For example, the preamble processor 1250 may provide a selection signal for changing the receiving electrode pair to the switch circuit 1221 during the switching times ts1 to ts8. The switch circuit 1221 may change the receiving electrode pair to receive the preamble on the basis of the selection signal.

Figure 6:
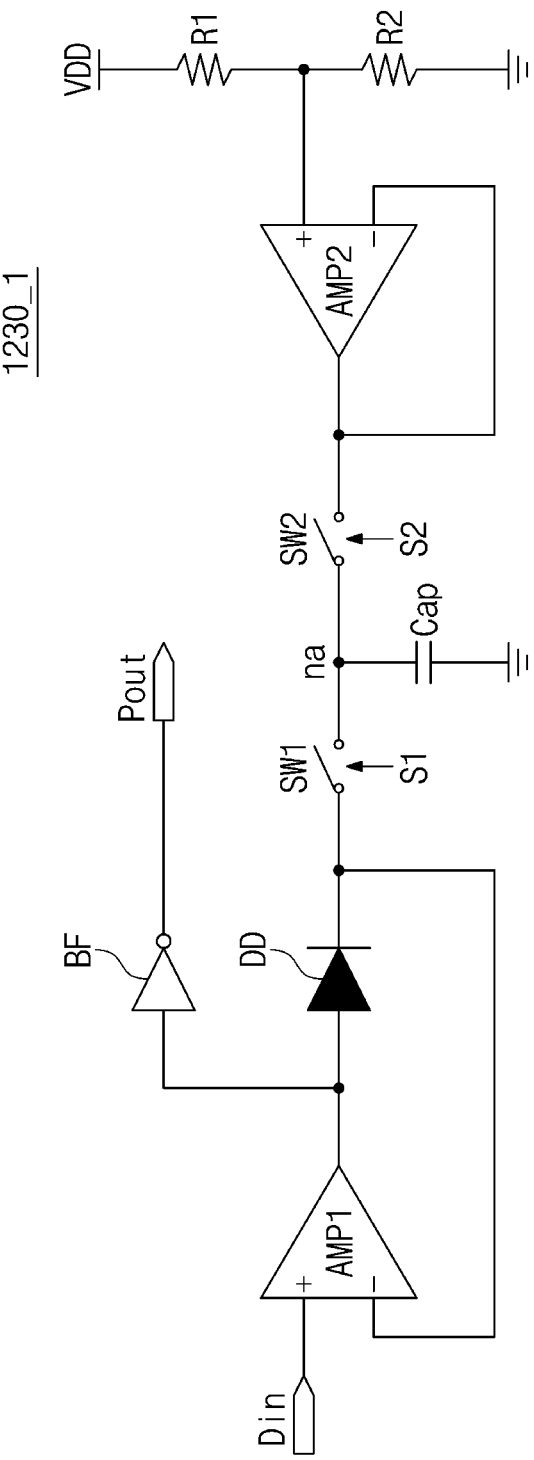
FIG. 6 is a circuit diagram illustrating an embodiment of a valid signal detection circuit of FIG. 3.

FIG. 6 is a circuit diagram illustrating an embodiment of the valid signal detection circuit of FIG. 3. In relation to FIG. 6, the valid signal detection circuit 1230_1 may include first and second amplifiers AMP1 and AMP2, a diode DD, first and second switches SW1 and SW2, a capacitor Cap, first and second resistors R1 and R2, and a buffer BF. The valid signal detection circuit 1230_1 may be understood as one embodiment in which the reference voltage and input data are compared to output the pulses, and the valid signal detection circuit 1230 of FIG. 3 will not be limited to the circuit structure of FIG. 6. For convenience of explanation, FIG. 6 will be described with reference to the reference numerals of FIG. 3.

When the input data is larger than the reference voltage, the first amplifier AMP1 may output the pulses Pout. The first amplifier AMP1 includes a first input terminal configured to receive the input data Din, a second input terminal connected to the diode DD and the first switch SW1, and an output terminal. The pulses Pout may be output through the output terminal of the first amplifier APM1 on the basis of the potential difference between the first and second input terminals. The pulses Pout may be provided to the preamble processor 1250 through the buffer BF. The preamble processor 1250 may count the number of pulses Pout to determine the validity of the receiving electrode pair having received the preamble.

The diode DD includes an input terminal connected to the output terminal of the first amplifier AMP1, and an output terminal connected to the second input terminal of the first amplifier AMP1 and one terminal of the first switch SW1. When a voltage level of the input terminal of the diode DD is higher than that of the output terminal of the diode DD, a voltage level of the output terminal of the diode DD and the second input terminal of the first amplifier AMP1 may be increased to that of the input terminal of the diode DD. When the voltage level of the input terminal of the diode DD is lower than that of the output terminal of the diode DD, the voltage level of the output terminal of the diode DD may not be decreased to that of the input terminal of the diode DD.

The second amplifier AMP2 may output the reference voltage. A voltage VDD may be divided by the first resistor R1 and the second resistor R2. The second amplifier AMP2 may include a first input terminal configured to receive the divided VDD, and a second terminal and an output terminal connected to each other. The output terminal of the second amplifier AMP2 may be connected to the second switch SW2.

The first switch SW1 may be turned on so as to provide the reference voltage to the input terminal of the first amplifier AMP1 at the time of receiving the preamble. The first switch SW1 may include one terminal connected to the second input terminal of the first amplifier AMP1 and the output terminal of the diode DD, and the other terminal connected to a node na. The second switch SW2 and the capacitor Cap are connected to the node na. When the received preamble has a higher voltage level than the reference voltage, the voltage level of the preamble may be applied to the capacitor Cap through the turned-on switch SW1. When the received preamble has a lower level than the reference voltage, the voltage level applied to the capacitor Cap may be maintained as the reference voltage. During the switching time, the first switch may be turned off. In this case, the voltage level applied to the capacitor Cap may be reset to the reference voltage. The first switch SW1 may be turned on or off on the basis of a first switch signal S1, and the first switch signal S1 may be generated by, for example, the preamble processor 1250.

The second switch SW2 may be turned on so that the reference voltage is stored in the capacitor Cap during the switching time. The second switch SW2 may include one terminal connected to the node na, and the other terminal connected to the output terminal of the second amplifier AMP2. At the time of receiving the preamble, the second switch SW2 may be turned off. In this case, the voltage level applied to the capacitor Cap may not be fixed to the reference voltage, and may be changed according to the generation or not of the pulses Pout. During the switching time, since the second switch SW2 is turned on, the voltage applied to the capacitor Cap may be reset to the reference voltage. The second switch SW2 may be turned on or off on the basis of a second switch signal S2, and the second switch signal S2 may be generated by, for example, the preamble processor 1250.

Figure 7:
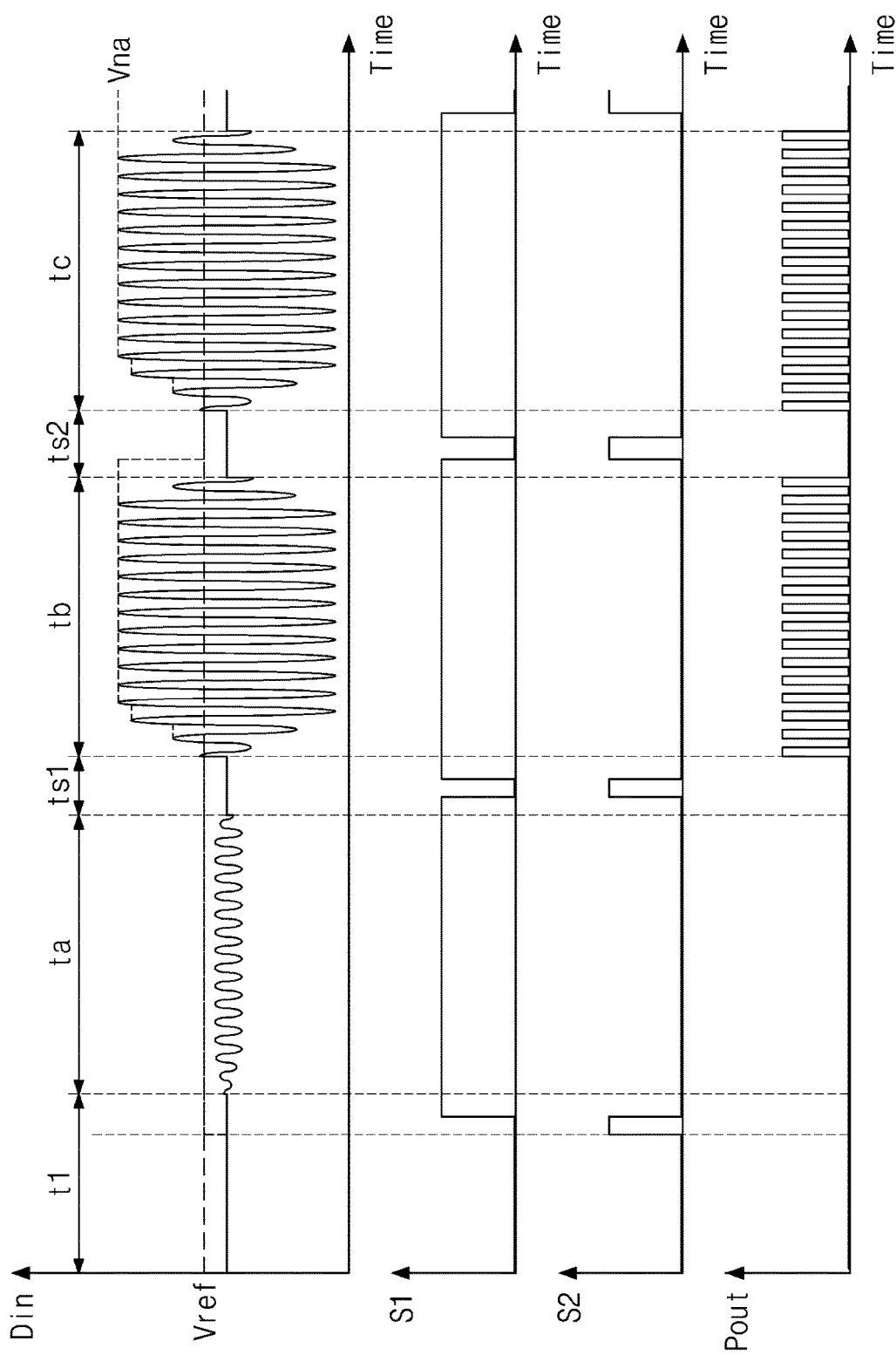
FIG. 7 is a graph for explaining generation of pulses according to input data in the valid signal detection circuit of FIG. 6.

FIG. 7 is a graph for explaining the generation of the pulses according to the input data in the valid signal detection circuit of FIG. 6. In FIG. 7, the magnitudes of the input data Din, the first switch signal S1, the second switch signal D2, and the pulses Pout are illustrated according to the flow of time. A horizontal axis may denote time, and a vertical axis may denote respective voltage levels of the input data Din, the first switch signal S1, the second switch signal D2, and the pulses Pout. The time of the horizontal axis may be divided into a first preamble reception time ta, a first switching time is 1, a second preamble reception time tb, a second switching time ts2, and a third preamble reception time tc. For convenience of explanation, FIG. 7 will be described with reference to the reference numerals of FIG. 6.

The first time t1 is a time during which the preamble and image data are not received, and corresponds to the first time t1 of FIG. 4. Before a termination time point of the first time t1, a first receiving electrode pair configured to receive a first preamble may be selected. For example, the first receiving electrode pair may be a combination of the first receiving electrode 1211 and the second receiving electrode 1212 of FIG. 3. As the second switch signal S2 is increased to a high level, the second switch SW2 is turned on, and a node voltage Vna corresponding to a both-terminal voltage of the capacitor Cap may become identical to the reference voltage Vref. Then, the second switch signal S2 is decreased to a low level to turn off the second switch SW2, and the first switch signal S1 is increased to a high level to turn on the first switch SW1. Here, the reference voltage Vref may be provided to the second input terminal of the first amplifier AMP1.

During the first preamble reception time ta, the valid signal detection circuit 1230_1 receives the input data Din corresponding to the first preamble. When the peak value of the input data Din is smaller than the reference voltage Vref, the first amplifier AMP1 may not output the pulses Pout, and the node voltage Vna may maintain the reference voltage Vref. During the first switching time ts1, as the first switch signal S1 is changed to a low level and the second switch signal S2 is changed to a high level, the reference voltage Vref is applied to the capacitor Cap. In addition, a second electrode pair configured to receive a second preamble may be selected. The second receiving electrode pair is different from the first receiving electrode pair.

During the second preamble reception time tb, the valid signal detection circuit 1230_1 receives the input data Din corresponding to the second preamble. When the peak value of the input data Din is larger than the reference voltage Vref, the first amplifier AMP1 may output the pulses Pout. In this case, a voltage level increased by the pulses Pout is transferred to the node na through the diode DD, and the node voltage Vna may be increased to a voltage level corresponding to the peak value of the input data Din. The increased node voltage Vna may be maintained till the second preamble reception time tb is terminated. The number of pulses Pout corresponds to the number of peak values having the voltage level larger than the reference voltage Vref. When the number of pulses Pout is larger than (or equal to) a reference number, the second receiving electrode pair is determined to be valid.

During the second switching time ts2, as the first switch signal S1 is changed to a low level and the second switch signal S2 is changed to a high level, a node voltage Vna that is a voltage stored in the capacitor Cap is reset to the reference voltage Vref. In addition, a third electrode pair configured to receive a third preamble may be selected. The third receiving electrode pair is different from the first and second receiving electrode pairs. During the third preamble reception time tc, the valid signal detection circuit 1230_1 receives the input data Din corresponding to the third preamble. As described about the first preamble reception time to and the second preamble reception time tb, when the peak value of the input data Din is larger than the reference voltage Vref, the pulses Pout are generated. In addition, when the peak value of the input data Din is smaller than the reference voltage Vref, the pulses Pout are not generated. According to the number of pulses Pout, the validity of the corresponding receiving electrode pair is determined.

Figure 8:
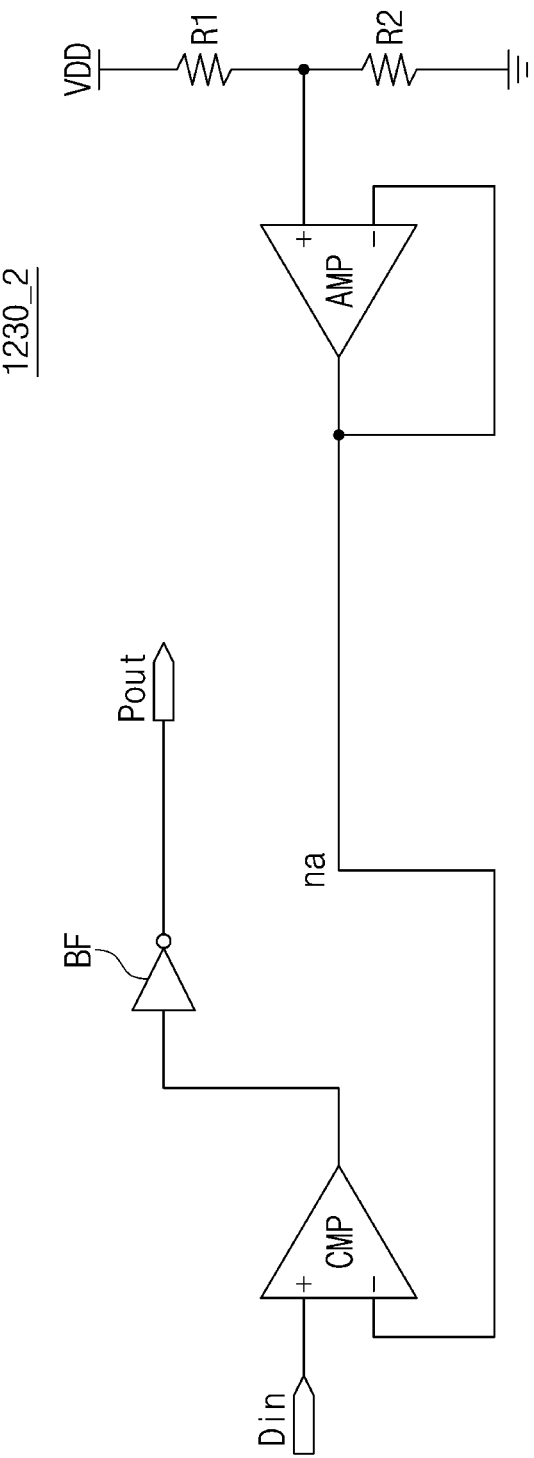
FIG. 8 is a circuit diagram illustrating another embodiment of a valid signal detection circuit of FIG. 3.

FIG. 8 is a circuit diagram illustrating another embodiment of the valid signal detection circuit of FIG. 3. In relation to FIG. 8, the valid signal detection circuit 1230_2 may include an amplifier AMP, a comparator CMP, first and second resistors R1 and R2, and a buffer BF. The valid signal detection circuit 1230_1 may be understood as one embodiment in which the reference voltage and input data are compared to output pulses, and the valid signal detection circuit 1230 of FIG. 3 will not be limited to the circuit structure of FIG. 8. For convenience of explanation, FIG. 8 will be described with reference to the reference numerals of FIG. 3.

When the input data is larger than the reference voltage, the comparator CMP may output the pulses Pout. The comparator CMP includes a first input terminal configured to receive the input data Din, a second input terminal configured to receive the reference voltage, and an output terminal.

The pulses Pout may be output through the output terminal of the comparator CMP on the basis of the potential difference between the first and second input terminals. The pulses Pout may be provided to the preamble processor 1250 through the buffer BF. The preamble processor 1250 may count the number of pulses Pout to determine the validity of the receiving electrode pair having received the preamble.

The amplifier AMP, the first resistor R1 and the second resistor R2 may be configured to output the reference voltage as the second amplifier AMP2, the first resistor R1 and the second resistor R2 of FIG. 6. The amplifier AMP may output the reference voltage to the second input terminal of the comparator CMP on the basis of a voltage VDD divided by the first and second resistors R1 and R2.

Figure 9:
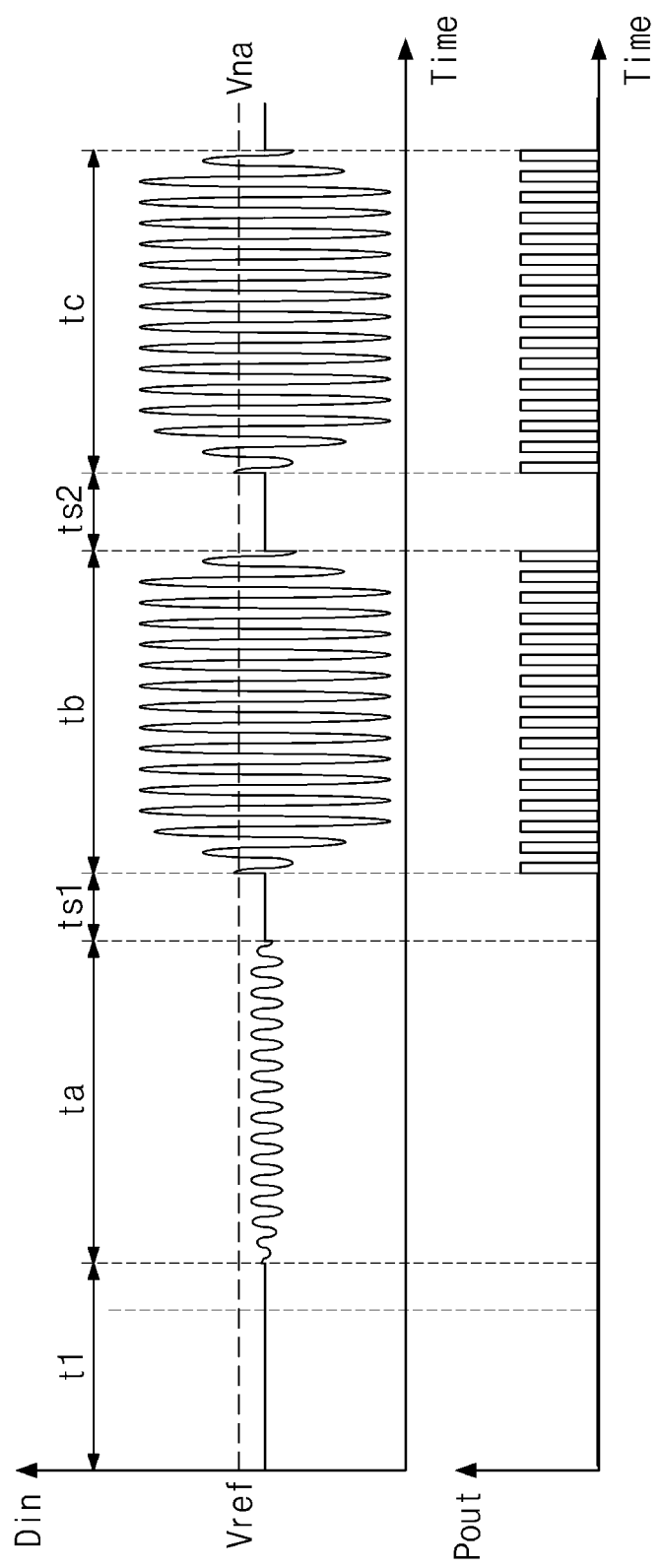
FIG. 9 is a graph for explaining generation of pulses according to input data in the valid signal detection circuit of FIG. 8.

FIG. 9 is a graph for explaining the generation of the pulses according to the input data in the valid signal detection circuit of FIG. 8. In relation to FIG. 9, the magnitudes of the input data Din and the pulses Pout are illustrated according to the flow of time. A horizontal axis may denote time, and a vertical axis may denote respective voltage levels of the input data Din and the pulses Pout. For convenience of explanation, FIG. 9 will be described in comparison with the graph of FIG. 7 and with reference to the reference numerals of FIG. 8.

The time of the horizontal axis may be divided into a first preamble reception time ta, a first switching time is 1, a second preamble reception time tb, a second switching time ts2, and a third preamble reception time tc. The times respectively correspond to the first time t1, the first preamble reception time ta, the first switching time ts1, the second preamble reception time tb, the second switching time ts2, and the third preamble reception time tc of FIG. 7, and thus detailed descriptions thereabout will be omitted.

The node voltage Vna is applied to the node na connected to the second input terminal of the comparator CMP. Unlike FIG. 7, the node voltage Vna is fixed to the reference voltage Vref. When the peak value of the input data is larger than the reference voltage Vref, the pulses Pout are generated, and when the peak value of the input data Din is smaller than the reference voltage Vref, the pulses Pout are not generated. In other words, the pulses Pout generated according to the input data Din may be substantially the same as those in FIG. 7.

Figure 10:
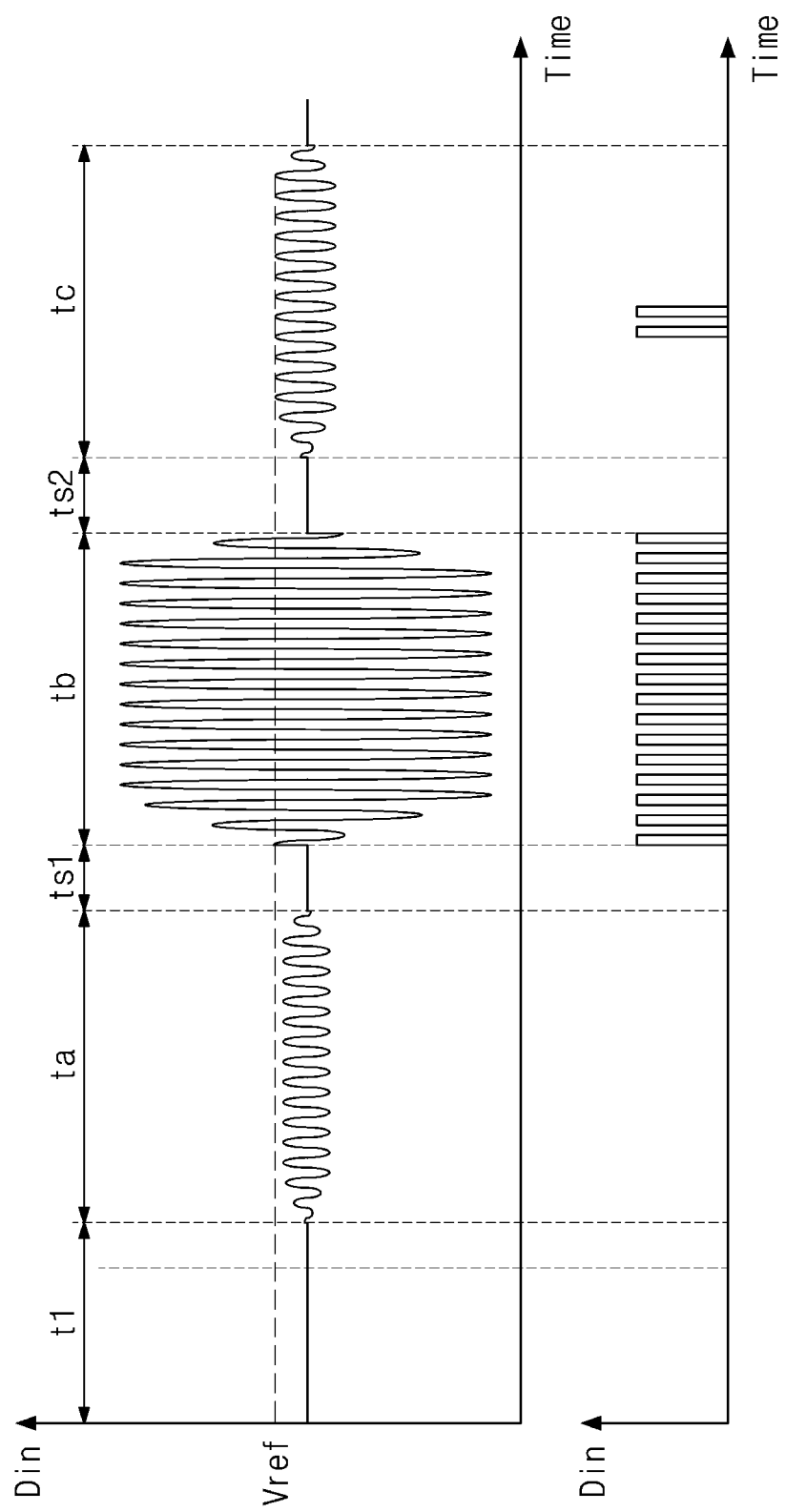
FIG. 10 is a graph for explaining generation of pulses according to input data in the valid signal detection circuit of FIG. 3.

FIG. 10 is a graph for explaining the generation of the pulses according to the input data in the valid signal detection circuit of FIG. 3. In relation to FIG. 10, the magnitudes of the input data Din and the pulses Pout are illustrated according to the flow of time. A horizontal axis may denote time, and a vertical axis may denote respective voltage levels of the input data Din and the pulses Pout. Like FIG. 7 or FIG. 9, the time of the horizontal axis may be divided into a first time t1, a first preamble reception time ta, a first switching time ts1, a second preamble reception time tb, a second switching time ts2, and a third preamble reception time tc.

The preamble processor 1250 may count the number of pulses Pout to determine the validity of a receiving electrode pair having received the preamble. When the number of pulses Pout is within a reference range, the preamble processor 1250 may determine the receiving electrode pair to be valid. For example, the reference range is assumed to be 14 to 16. When the number of pulses Pout is smaller than 14, the preamble processor 1250 may determine the corresponding receiving electrode pair to be one through which it is difficult to identify the image data. When the number of pulses Pout exceeds 16, the preamble processor 1250 may determine the corresponding receiving electrode pair to be one through which it is highly possible that a noise is reflected to and distorts the image data.

As in the first preamble reception time ta, when the peak value of the input data Din is smaller than the reference voltage Vref, the pulses Pout are not generated. In this case, the number of pulses Pout is 0, and thus the preamble processor 1250 may determine the first receiving electrode pair not to be valid. Accordingly, the first receiving electrode pair is not selected as the final electrode pair.

As in the second preamble reception time tb, when the peak value of the input data Din is larger than the reference voltage Vref, the pulses Pout are generated. In this case, the number of pulses Pout is 16, and thus the preamble processor 1250 may determine the second receiving electrode pair to be valid. Accordingly, the second receiving electrode pair may be selected as the final electrode pair according to a correlation value calculation result.

As in the third preamble reception time tc, when a part of the peak value of the input data Din is larger than the reference voltage Vref, and another part is smaller than the reference voltage Vref, the pulses Pout may be generated with less frequency. In this case, the number of pulses Pout is 2, and thus the preamble processor 1250 may determine the third receiving electrode pair not to be valid. Accordingly, the third receiving electrode pair is not selected as the final electrode pair.

Since the preamble processor 1250 does not measure the voltage level of the received preamble but only counts the number of pulses, a separate circuit configured to measure the voltage level may not be required. For example, in order to measure the voltage level of the preamble, a digital-to-analog converter may not be required. Accordingly, the configuration for selecting the receiving electrode pair may be simplified, and the validity for each receiving electrode pair combination may be easily determined.

Figure 11:
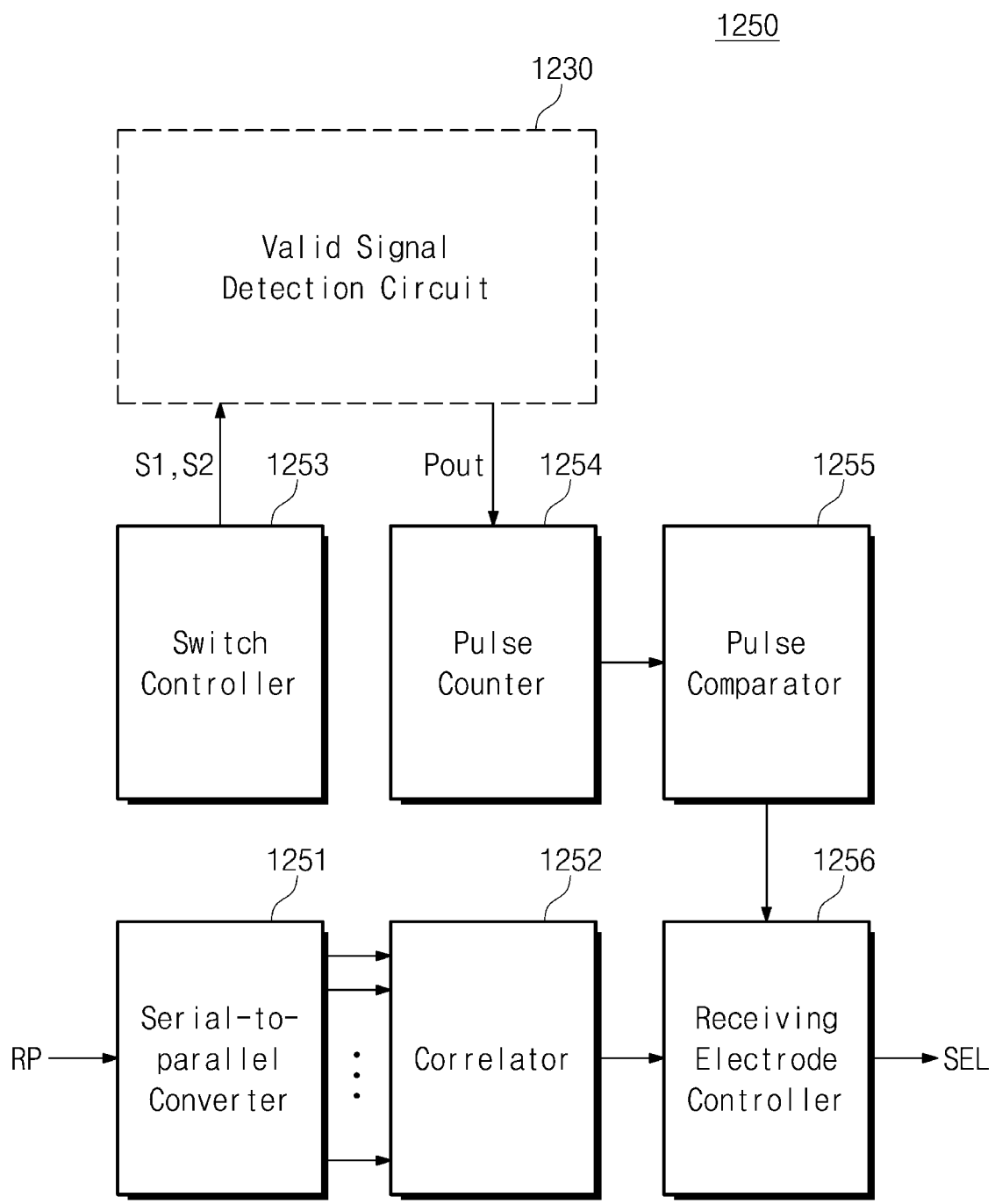
FIG. 11 is an exemplary block diagram of a preamble processor of FIG. 3.

FIG. 11 is an exemplary block diagram of the preamble processor of FIG. 3. In relation to FIG. 11, the preamble processor 1250 includes a serial-to-parallel converter 1251, a correlator 1252, a switch controller 1253, a pulse counter 1254, a pulse comparator 1255, and a receiving electrode controller 1256. The preamble processor 1250 may be understood as one embodiment in which the final electrode pair is selected through the validity and correlation value of the preamble, and the preamble processor 1250 of FIG. 3 will not be limited to the structure of FIG. 11.

The serial-to-parallel converter 1251 converts a preamble RP provided as serial data into parallel data. The serial-to-parallel converter 1251 receives the preamble recovered by the clock data recovery circuit 1227 of FIG. 3. In order to compare the patterns for calculating a correlation value, the preamble RP received as serial data in a 1 bit unit is converted to parallel data and output to the correlator 1252.

The correlator 1252 calculates a correlation value of the preamble RP converted to the parallel data. The correlator 1252 may compare a preset reference preamble with the received preamble RP to calculate a similarity. For example, the preamble RP may include a plurality of bit values, and the correlator 1252 may calculate the correlation value on the basis of a degree of matching of bit values included in the reference preamble and the bit values included in the preamble RP. As the similarity between the reference preamble and the preamble RP is higher, the correlation value may be larger. The correlator 1252 may calculate the correlation value of the preamble RP for each receiving electrode pair combination, and the correlation values of the receiving electrode pairs may be stored in a memory (not shown).

The switch controller 1253 may generate the first switch signal S1 and the second switch signal S1 for controlling the valid signal detection circuit 1230. For example, when the valid signal detection circuit 1230 is the same as the valid signal detection circuit 1230_1 of FIG. 6, the switch controller 1253 may generate the first and second switch signals S1 and S2 for determining the turn-on or turn-off of the first switch SW1 and the second switch SW2. The waveforms of the first and second switch signals S1 and S2 may be respectively the same as those shown in FIG. 7. However, when the valid signal detection circuit 1230 is identical to the valid signal detection circuit 1230_2 of the FIG. 8, the switch controller 1253 may not be included in the preamble processor 1250.

The pulse counter 1254 may count the number of pulses Pout generated by the valid signal detection circuit 1230. The pulse counter 1254 may count the number of pulses Pout generated on the basis of the preamble provided from the selected receiving electrode pair during the preamble reception time. The counted number of pulses Pout may be provided to the pulse comparator 1255. The pulse counter 1254 may count the number of pulses Pout for each receiving electrode pair combination, and the counted value for each receiving electrode pair combination may be stored in the memory (not shown).

The pulse comparator 1255 may determine whether the number of pulses Pout is within the reference range. For example, the pulse comparator 1255 may compare the number of pulses Pout with the reference number, and provide the comparison result to the receiving electrode controller 1256. For example, the reference number may be defined as the minimum number of pulses Pout for determining the image data to be identifiable. In this case, when the number of pulses Pout is larger than the reference number, the receiving electrode pair receiving the corresponding preamble may be determined to be valid. The pulse comparator 1255 may generate a result of comparing the number of pulses Pout and the reference number for each receiving electrode pair combination, and store the generated result in the memory (not shown).

The receiving electrode controller 1256 may select the final electrode pair on the basis of the correlation value and validity of the preamble. In order to select the final electrode pair, the receiving electrode controller 1256 may control the switch circuit 1221 of FIG. 3 in order to receive the preamble for each receiving electrode pair combination. Then, the correlation and validity may be determined for each of the receiving electrode pairs. The receiving electrode controller 1256 may receive the correlation value of the preamble for each of receiving electrode pairs from the correlator 1252. The receiving electrode controller 1256 may receive, from the pulse comparator 1255, the result of determining whether the number of pulses Pout is within the reference range. The receiving electrode controller 1256 may select the final electrode pair according to the determination result.

The receiving electrode controller 1256 may generate a selection signal SEL for selecting the final electrode pair. The selection signal SEL may be provided to the switch circuit 1221 of FIG. 3. The capsule endoscopic receiving device 1200 may receive the image data through the final electrode pair. The receiving electrode controller 1256 may generate the selection signal SEL so as to select the final electrode pair from among the receiving electrode pairs having the validity. For example, the receiving electrode controller 1256 may select, as the final electrode pair, a receiving electrode pair having the largest correlation value from among the receiving electrode pairs having the validity.

Figure 12:
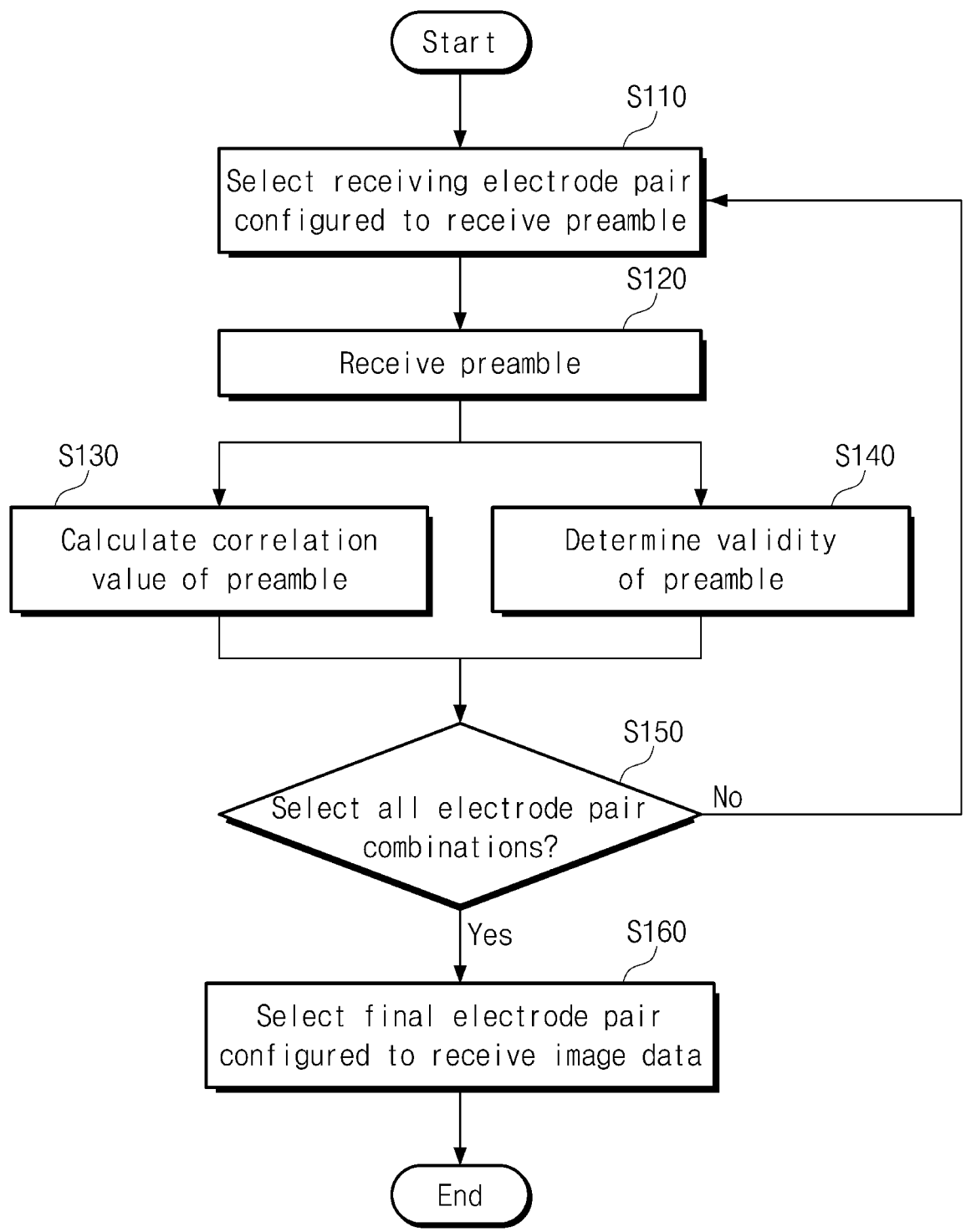
FIG. 12 is a flowchart of an operation method of the capsule endoscopic receiving device according to an embodiment of the inventive concept.

FIG. 12 is a flowchart of an operation method of the capsule endoscopic receiving device according to an embodiment of the inventive concept. In relation to FIG. 12, the operation method of the capsule endoscopic receiving device is executed in the capsule endoscopic receiving device 1200 of FIG. 3. For convenience of explanation, FIG. 12 will be described with reference to the reference numerals of FIG. 3.

In operation S110, the capsule endoscopic receiving device 1200 selects a receiving electrode pair configured to receive the preamble. The preamble may be received for each receiving electrode pair combination. The preamble processor 1250 may continuously change the receiving electrode pair to be selected in order to receive the preambles for all the receiving electrode pair combinations.

In operation S120, the capsule endoscopic receiving device 1200 may receive the preamble, which is a differential signal, from the selected receiving electrode pair. Under the control of the preamble processor 1250, the switch circuit 1221 may be electrically connected to two receiving electrodes among the first to nth receiving electrodes 1211 to 121n, and receive the preamble.

In operation S130, the capsule endoscopic receiving device 1200 may calculate the correlation value of the preamble. The preamble processor 1250 may calculate the correlation value on the basis of the similarity between the preamble received from the selected receiving electrode pair and the reference preamble. For example, as the degree of matching between the received preamble and the reference preamble is higher, the correlation value may be higher.

In operation S140, the capsule endoscopic receiving device 1200 may determine the validity of the preamble or the receiving electrode pair receiving the preamble. The validity signal detection circuit 1230 may compare the reference voltage and the input data generated on the basis of the voltage level of the received preamble. When the peak value of the input data is larger than the reference voltage, the valid signal detection circuit 1230 may generate the pulses. The preamble processor 1250 may count the number of the generated pulses, and when the number of pulses is within the reference range, the receiving electrode pair having received the preamble may be determined to be valid.

In operation S150, the capsule endoscopic receiving device 1200 may determine whether all receiving electrode pair combinations are selected. When all the receiving electrode pair combinations are not selected with respect to the first to nth receiving electrodes 1211 to 121n, operation S110 is performed again. In this case, in operation S110, a receiving electrode pair that has not been selected before may be selected. Then, operations S120 to S140 are performed. When all the receiving electrode pair combinations are selected, operation S160 is performed to select the final electrode pair.

In operation S160, the capsule endoscopic receiving device 1200 selects the final electrode pair configured to select the image data. The preamble processor 1250 may select the final electrode pair on the basis of the correlation value of the preamble for each receiving electrode pair, which is determined in operation S130, and the validity for each receiving electrode pair, which is determined in operation S140. The preamble processor 1250 may select the final electrode pair from among the receiving electrode pairs having the validity. For example, the preamble processor may select, as the final electrode pair, a receiving electrode pair having received the preamble having the largest correlation value from among the receiving electrode pairs having the validity. The preamble processor 1250 may provide the selection signal to the switch circuit 1221 in order to receive the image data through the final electrode pair, and receive the image data through receiving electrodes corresponding to the final electrode pair.

Figure 13:
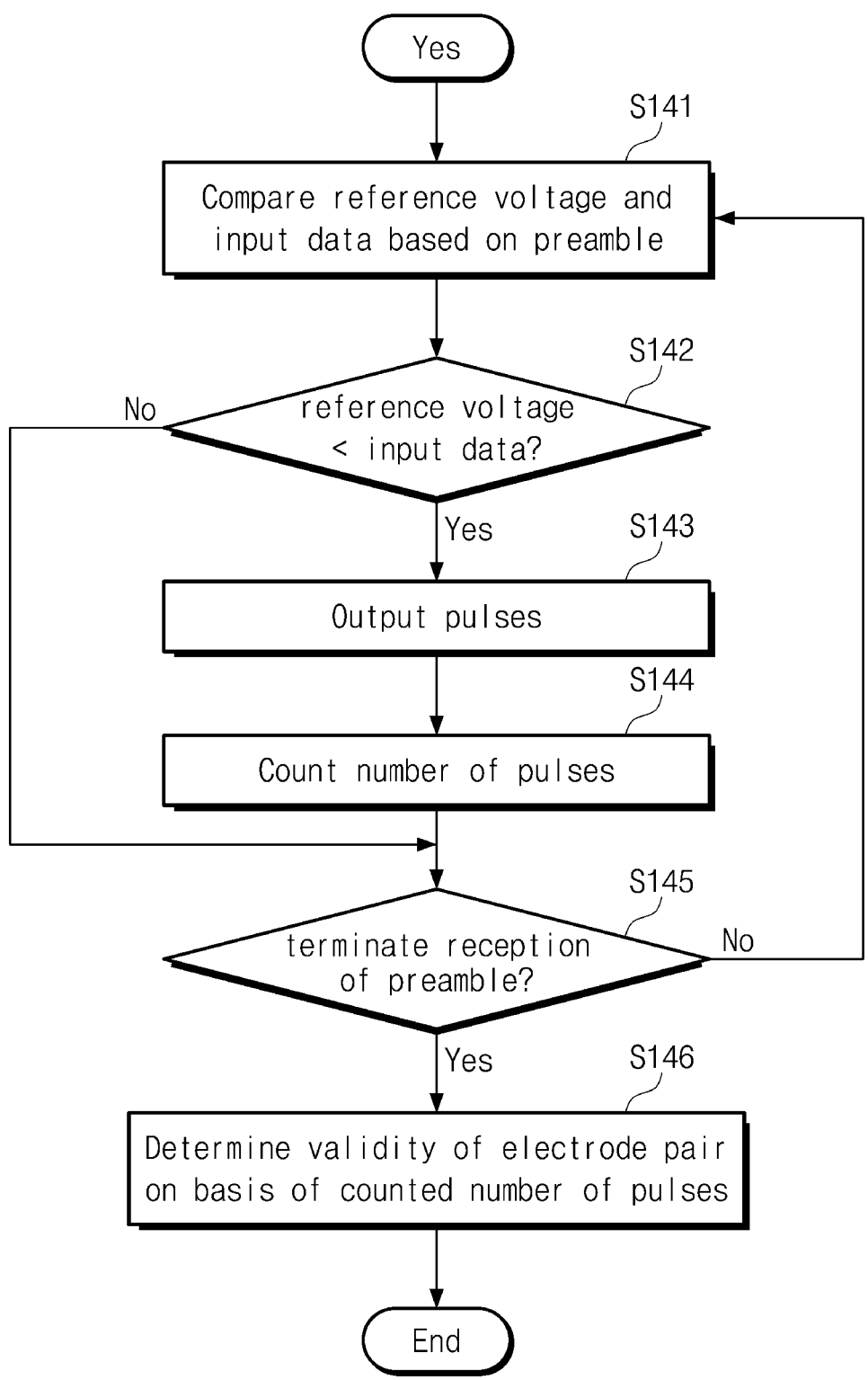
FIG. 13 is an embodied flowchart of operation S140 of FIG. 12.

FIG. 13 is an embodied flowchart of an operation S140 of FIG. 12. In relation to FIG. 13, operation S140 may be performed in the valid signal detection circuit 1230 and the preamble processor 1250 of FIG. 3. For convenience of explanation, FIG. 13 will be described with reference to the reference numerals of FIG. 3.

In operation S141, the valid signal detection circuit 1230 may compare the reference voltage and the input data generated on the basis of the preamble. The voltage level of the input data depends on that of the preamble. In operation S142, as a result of comparing the input data and the reference voltage, when the input data has a larger voltage level than the reference voltage, operation S143 is performed. When the input data does not have the larger voltage level than the reference voltage, operation S145 is performed.

In operation S143, the valid signal detection circuit 1230 outputs the pulses. When the peak value of the input data is larger than the reference voltage, the pulses are output. The pulses may be output to the preamble processor 1250. In operation S144, the preamble processor 1250 may count the number of pulses. The number of pulses may be counted during a time in which the preamble is received through the selected receiving electrode pair.

In operation s145, the preamble processor 1250 may determine whether the reception of the preamble is terminated at the selected receiving electrode pair. For example, the preamble processor 1250 may determine whether the reception of the preamble is terminated on the basis of information on the time at which the preamble included in the control frame is provided.

In operation S146, the preamble processor 1250 may determine the validity of the receiving electrode pair on the basis of the counted number of pulses. When the counted number of pulses is within the reference range, the preamble processor 1250 may determine the receiving electrode pair to be valid. Otherwise, the preamble processor 1250 may determine the receiving electrode pair not to be valid, and may not select the receiving electrode pair as the final electrode pair.

The capsule endoscopic receiving device, the capsule endoscope system including the same, and the operation method of the capsule endoscopic receiving device according to the embodiments of the inventive concept may secure stability of receiving image data by selecting an optimal receiving electrode pair using the voltage level and correlation value of the preamble.

The foregoing description is about detailed examples for practicing the inventive concept. The present disclosure includes not only the above-described embodiments but also simply changed or easily modified embodiments. In addition, the present disclosure may also include technologies obtained by easily modifying and practicing the above-described embodiments.

What is claimed is:

1. A capsule endoscopic receiving device comprising:
   an analog front end configured to receive a preamble from one receiving electrode pair from among a plurality of receiving electrodes;
   a valid signal detection circuit configured to compare a reference voltage with input data generated on a basis of a voltage level of the preamble; and
   a preamble processor configured to select a final electrode pair configured to receive image data on a basis of a correlation value of the preamble and a comparison result of the input data and the reference voltage;
   wherein, when the input data is larger than the reference voltage, the valid signal detection circuit outputs pulses to the preamble processor; and
   wherein the preamble processor is further configured to count a number of the pulses to determine validity of a receiving electrode pair having received the preamble.

2. The capsule endoscopic receiving device of claim 1, wherein the preamble processor selects the final electrode pair from among receiving electrode pairs having the validity.

3. The capsule endoscopic receiving device of claim 2, wherein the preamble processor selects, as the final electrode pair, a receiving electrode pair corresponding to a preamble having a largest correlation value from among the receiving electrode pairs having the validity.

4. The capsule endoscopic receiving device of claim 1, wherein the valid signal detection circuit comprises:
   an amplifier configured to output the pulses on a basis of the input data and the reference voltage;
   a diode configured to provide a voltage generated on the basis of the pulses or the reference voltage to the amplifier; and
   a capacitor configured to store the voltage,
   wherein, when the pulses are output, the voltage is generated on a basis of a peak value of the pulses, and, when the pulses are not output, the voltage is the reference voltage.

5. The capsule endoscopic receiving device of claim 4, wherein the valid signal detection circuit comprises:
   a first switch configured to electrically connect the capacitor and the diode, while the receiving electrode pair receives the preamble; and
   a second switch configured to provide the reference voltage to the capacitor, while the receiving electrode pair does not receive the preamble.

6. The capsule endoscopic receiving device of claim 1, wherein the valid signal detection circuit comprises a comparator configured to generate the pulses, when the input data is larger than the reference voltage.

7. The capsule endoscopic receiving device of claim 1, wherein the preamble processor comprises:
   a pulse counter configured to count the number of pulses;
   a pulse comparator configured to compare the number of pulses and a reference number;
   a correlator configured to calculate the correlation value on a basis of a similarity between the preamble and a reference preamble; and
   a receiving electrode controller configured to generate a selection signal for selecting the final electrode pair on a basis of the correlation value and a result of comparing the number of pulses with the reference number.

8. The capsule endoscopic receiving device of claim 1, wherein the analog front end comprises:
   a switch circuit configured to receive the preamble from a receiving electrode pair selected by the preamble processor;
   an amplifier configured to amplify the preamble to generate the input data; and
   a clock data recovery circuit configured to recover a clock and data for the preamble on a basis of the input data.

9. The capsule endoscopic receiving device of claim 1, further comprising:
a second valid signal detection circuit configured to compare the input data with a second reference voltage that is different from the reference voltage,
wherein the preamble processor selects the final electrode pair further on a basis of a result of comparing the input data with the second reference voltage.

10. A capsule endoscope system comprising:
a capsule endoscopic transmission circuit configured to generate a preamble and image data; and
a capsule endoscopic receiving device configured to receive the preamble through a living body for each receiving electrode pair combination for a plurality of receiving electrodes, and to select a final electrode pair configured to receive the image data on a basis of a received voltage level of the preamble and a correlation value of the preamble;
wherein the capsule endoscopic receiving device comprises:
a valid signal detection circuit configured to generate pulses, when the received voltage level of the preamble is larger than that of a reference voltage; and
a preamble processor configured to count a number of the pulses to determine validity of a receiving electrode pair having received the preamble.

11. The capsule endoscope system of claim 10, wherein the capsule endoscopic receiving device comprises:
a digital reception circuit configured to select the final electrode pair on a basis of the number of pulses and the correlation value.

12. The capsule endoscope system of claim 10, wherein the capsule endoscopic receiving device calculates the correlation value on a basis of a similarity between the preamble and a reference preamble.

13. The capsule endoscope system of claim 10, wherein, from among receiving electrode pair combinations, the capsule endoscopic receiving device selects, as the final electrode pair, a receiving electrode pair having received a preamble of which the received voltage level is larger than the reference voltage and the correlation value is a largest.

14. The capsule endoscope system of claim 10, wherein the capsule endoscopic transmission circuit comprises:
an image sensor configured to generate the image data on a basis of sensed light;
an image data generator configured to generate an image frame comprising the image data; and
a transmission circuit configured to generate a control frame comprising the preamble, and transmit a transmission frame comprising the control frame and the image frame to the living body through a transmission electrode.

15. An operation method of a capsule endoscopic receiving device, the operation method comprising:
selecting a first receiving electrode pair from among a plurality of receiving electrodes during a first switching time;
receiving a preamble generated from a capsule endoscope through the first receiving electrode pair during a preamble reception time after the first switch time;
determining validity of the preamble on a basis of a voltage level of the preamble received through the first receiving electrode pair;
calculating a correlation value corresponding to the first receiving electrode pair on a basis of a similarity between the preamble received through the first receiving electrode pair and a reference preamble;
selecting a second receiving electrode pair that is different from the first receiving electrode pair during a second switching time after the preamble reception time; and
selecting a final electrode pair from among the plurality of receiving electrodes on a basis of the validity and the correlation value;
wherein the determining of the validity comprises:
comparing a reference voltage and input data generated on a basis of the voltage level of the preamble;
generating pulses, when the input data is larger than the reference voltage;
counting a number of pulses; and
determining the validity of the first receiving electrode pair on a basis of the number of pulses.

16. The operation method of claim 15, further comprising:
receiving image data generated from the capsule endoscope through the final electrode pair,
wherein the final electrode pair is selected from among receiving electrode pairs that have received the preamble having the validity.

17. The operation method of claim 15, further comprising:
receiving the preamble through the second receiving electrode pair during a second preamble reception time after the second switching time;
determining validity of the second receiving electrode pair on a basis of a voltage level of the preamble received through the second receiving electrode pair;
calculating a correlation value corresponding to the second receiving electrode pair on a basis of a similarity between the reference preamble and the preamble received through the second receiving electrode pair; and
determining whether all electrode pair combinations for the plurality of receiving electrodes are selected.

18. The operation method of claim 15, wherein the receiving of the preamble comprises:
receiving, by the capsule endoscopic receiving device configured to contact a part of a body, the preamble transferred by adopting the body as a medium from the capsule endoscope configured to contact another part of the body.

* * * * *